United States Patent
Jeppesen et al.

(10) Patent No.: US 8,148,412 B2
(45) Date of Patent: Apr. 3, 2012

(54) HETEROAROMATIC GLUCOKINASE ACTIVATORS

(75) Inventors: Lone Jeppesen, Virum (DK); Marit Kristiansen, Soborg (DK)

(73) Assignee: Novo Nordisk A/S, Bagsvaerd (DK)

(*) Notice: Subject to any disclaimer, the term of this patent is extended or adjusted under 35 U.S.C. 154(b) by 277 days.

(21) Appl. No.: 11/791,200

(22) PCT Filed: Dec. 5, 2005

(86) PCT No.: PCT/EP2005/056473
§ 371 (c)(1),
(2), (4) Date: Nov. 13, 2007

(87) PCT Pub. No.: WO2006/058923
PCT Pub. Date: Jun. 8, 2006

(65) Prior Publication Data
US 2008/0139562 A1    Jun. 12, 2008

(30) Foreign Application Priority Data
Dec. 3, 2004  (DK) .................... 2004 01888

(51) Int. Cl.
*A61K 31/426* (2006.01)
*C07D 275/03* (2006.01)
*C07D 277/46* (2006.01)

(52) U.S. Cl. ......... 514/370; 514/372; 548/195; 548/214
(58) Field of Classification Search .................. 548/195, 548/214
See application file for complete search history.

(56) References Cited

U.S. PATENT DOCUMENTS

| | | | |
|---|---|---|---|
| 6,320,050 B1 * | 11/2001 | Bizzarro et al. | 544/332 |
| 6,610,846 B1 * | 8/2003 | Bizzarro et al. | 544/182 |
| 7,034,049 B1 | 4/2006 | Pevarello et al. | |
| 7,132,425 B2 | 11/2006 | Chen et al. | |
| 2004/0014968 A1 | 1/2004 | Bizzarro et al. | |
| 2004/0147748 A1 | 7/2004 | Chen et al. | |
| 2005/0176789 A1 * | 8/2005 | Ruah et al. | 514/370 |

FOREIGN PATENT DOCUMENTS

| | | |
|---|---|---|
| JP | 2002-540196 | 11/2002 |
| JP | 2003-507329 | 2/2003 |
| JP | 2003-531898 | 10/2003 |
| JP | 2003-532718 | 11/2003 |
| JP | 2003-532719 | 11/2003 |
| WO | WO 00/58293 | 10/2000 |
| WO | WO 01/83465 | 11/2001 |
| WO | WO 01/85706 | 11/2001 |
| WO | WO 01/85707 | 11/2001 |
| WO | WO 2004/002481 A1 | 1/2004 |
| WO | WO 2004/041813 * | 5/2004 |
| WO | WO 2004/052869 | 6/2004 |

OTHER PUBLICATIONS

Chipkin, S.R. et al., "Joslin's Diabetes Mellitus", 1994, pp. 97-115.
Printz, R.L. et al., "Mammalian Glucokinase", Annual Review of Nutrition, 1993, vol. 13, pp. 463-496.
Meglasson, M.D. et al., "New Perspectives on Pancreatic Islet Glucokinase", American Journal of Physiology, 1984, vol. 246, pp. E1-E13.
Grupe, A. et al., "Transgenic Knockouts Reveal a Critical Requirement for Pancreatic β Cell Glucokinase in Maintaining Glucose Homeostasis", Cell, 1995, vol. 83, pp. 69-78.
Liang, Y. et al., "Variable Effects of Maturity-Onset-Diabetes-of-Youth (MODY)-Associated Glucokinase Mutations on Substrate Interactions and Stability of the Enzyme", Biochemistry, 1995, vol. 309, pp. 167-173.
Glaser, B. et al., "Familial Hyperinsulinism Caused by an Activating Glucokinase Mutation", The New England Journal of Medicine, 1998, vol. 338, pp. 226-230.
Ferre, T. et al., "Evidence from Transgenic Mice that Glucokinase is Rate Limiting for Glucose Utilization in the Liver", The Faseb Journal, 1996, vol. 10, pp. 1213-1218.
Colowick, S.P., "The Enzymes", 1973, vol. 9, pp. 1-48.
Office Action dated Apr. 28, 2010 for copending European Application No. 05815875.9 filed Jun. 1, 2007 by Jeppesen et al.
Office Action dated Mar. 22, 2010 for copending European Application No. 05815875.9 filed Jun. 1, 2007 by Jeppsen et al.

* cited by examiner

*Primary Examiner* — Shawquia Young
(74) *Attorney, Agent, or Firm* — Rosemarie R. Wilk-Orescan

(57) ABSTRACT

The present invention describes 2,3-di-substituted N-heteroaromatic propionamides, of Formula (I) wherein the substitution at the 3-position is an optionally substituted phenyl ring and the substitution at the 2-position is an alkyl or cycloalkyl group; pharmaceutical compositions comprising the same; and, methods of using the same. The propionamides are glucokinase activators for the treatment of type II diabetes.

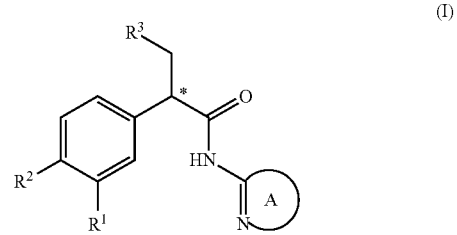

(I)

13 Claims, 1 Drawing Sheet

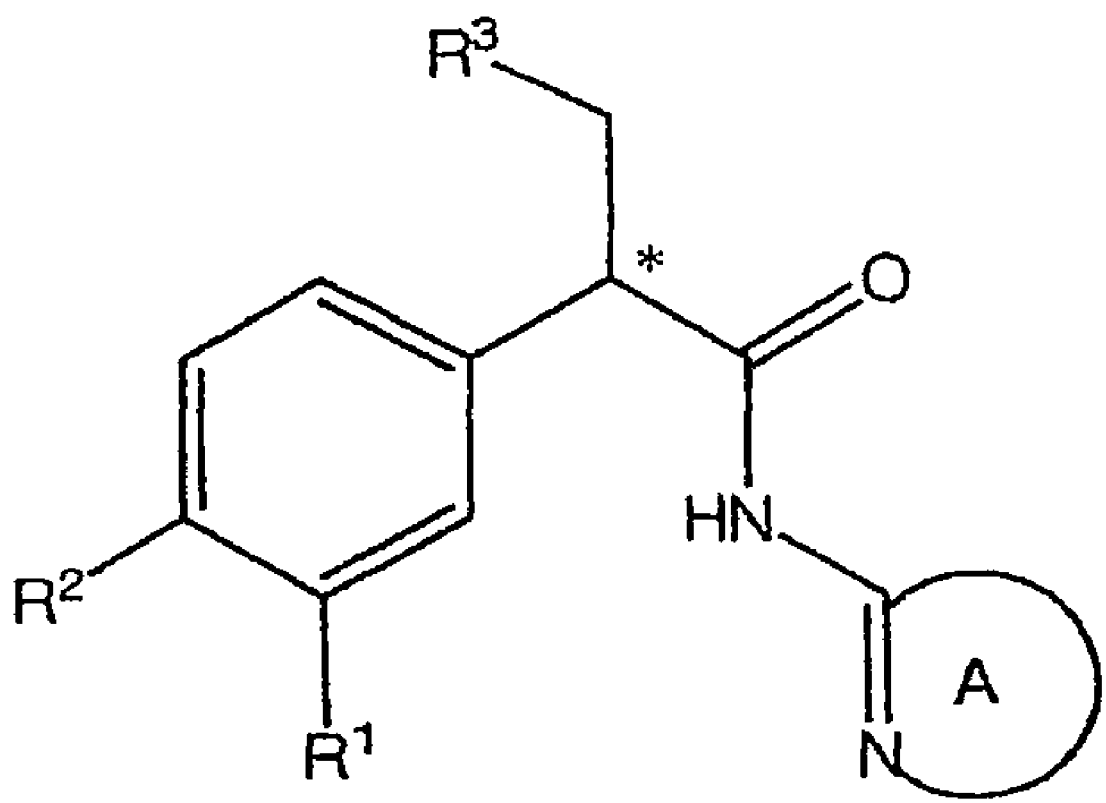

US 8,148,412 B2

HETEROAROMATIC GLUCOKINASE ACTIVATORS

CROSS-REFERENCE TO RELATED APPLICATIONS

This application is a 35 U.S.C. §371 National Stage application of International Patent Application PCT/EP2005/056473 (published as WO 2006/058923 A1), filed Dec. 5, 2005, which claimed priority of Danish Patent Application PA 2004 01888, filed Dec. 3, 2004.

FIELD OF THE INVENTION

The present invention relates to 2,3-di-substituted N-heteroaromatic propionamides, pharmaceutical compositions comprising the same, and methods of using the same. The propionamides are useful as glucokinase activators which increase insulin secretion in the treatment of type II diabetes.

BACKGROUND OF THE INVENTION

Glucokinase (GK) is one of four hexokinases that are found in mammals [Colowick, S. P., in The Enzymes, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. Amer. J. Physiol. 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes. Several GK activators are known, see, for example, US 2004/0014968 (Hofmann-La Roche Inc.) and WO 2004/002481 (Novo Nordisk A/S)

SUMMARY OF THE INVENTION

In an aspect, the present invention provides novel 2,3-di-substituted N-heteroaromatic propionamides or pharmaceutically acceptable salts thereof that are useful as glucokinase activators.

In another aspect, the present invention provides novel pharmaceutical compositions comprising a pharmaceutically acceptable carrier and a therapeutically effective amount of at least one of the compounds of the present invention or a pharmaceutically acceptable salt thereof.

In another aspect, the present invention provides a novel method of treating type II diabetes comprising administering to a patient in need thereof a therapeutically effective amount of at least one compound of the present invention or a pharmaceutically acceptable salt thereof.

In another aspect, the present invention provides a novel method of treating a condition or disease, comprising administering to a patient in need thereof a therapeutically effective amount of at least one compound of the present invention or a pharmaceutically acceptable salt thereof, wherein the condition or disorder is selected from a metabolic disorder, blood glucose lowering, hyperglycemia, impaired glucose tolerance (IGT), Syndrome X, Polycystic Ovarian Syndrome, impaired fasting glucose (IFG), type I diabetes, delaying the progression of impaired glucose tolerance (IGT) to type II diabetes, delaying the progression of non-insulin requiring type II diabetes to insulin requiring type II diabetes, dyslipidemia, hyperlipidemia, hypertension, treatment or prophylaxis of obesity, lowering of food intake, appetite regulation, regulating feeding behaviour, and enhancing the secretion of enteroincretins.

In another aspect, the present invention provides novel 2,3-di-substituted N-heteroaromatic propionamides for use in therapy.

In another aspect, the present invention provides the use of novel 2,3-di-substituted N-heteroaromatic propionamides for the manufacture of a medicament for the treatment of type II diabetes.

In another aspect, the present invention provides the use of novel 2,3-di-substituted N-heteroaromatic propionamides for the manufacture of a medicament for the treatment of a condition or disorder selected from a metabolic disorder, blood glucose lowering, hyperglycemia, impaired glucose tolerance (IGT), Syndrome X, Polycystic Ovarian Syndrome, impaired fasting glucose (IFG), type I diabetes, delaying the progression of impaired glucose tolerance (IGT) to type II diabetes, delaying the progression of non-insulin requiring type II diabetes to insulin requiring type II diabetes, dyslipidemia, hyperlipidemia, hypertension, treatment or prophylaxis of obesity, lowering of food intake, appetite regulation, regulating feeding behaviour, and enhancing the secretion of enteroincretins.

These and other objects, which will become apparent during the following detailed description, have been achieved by the inventors' discovery that compounds of formula I:

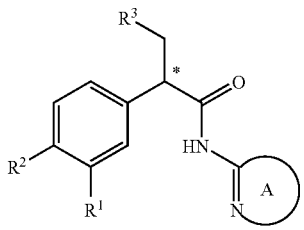

I wherein ring A is a 5-6 membered heteroaromatic ring, or pharmaceutically acceptable salts thereof, are expected to be effective glucokinase activators.

DETAILED DESCRIPTION OF THE INVENTION

In an embodiment, the present invention provides a novel compound of formula I:

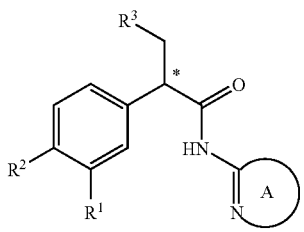

I wherein, the * indicates an asymmetric atom;
$R^1$ is selected from H, Cl, F, Br, I, $NH_2$, —NHOH, —CN, —$NO_2$, $C_{1-6}$ alkyl, —$OR^5$, —$C(O)OR^6$, perfluoro-$C_{1-6}$ alkyl, $C_{1-6}$ alkyl-S—, perfluoro-$C_{1-6}$ alkyl-S—, $C_{1-6}$ alkyl-$SO_2$—, perfluoro-$C_{1-6}$ alkyl-$SO_2$—, $C_{1-6}$ alkoxy-$C_{1-6}$ alkyl-$SO_2$—, $C_{1-6}$ alkyl-S(O)—, and —$SO_2NR^{13}R^{14}$;
$R^2$ is selected from H, Cl, F, Br, I, $NH_2$, —NHOH, —CN, —$NO_2$, $C_{1-6}$ alkyl, —$OR^5$, —$C(O)OR^6$, perfluoro-$C_{1-6}$ alkyl, $C_{1-6}$ alkyl-S—, perfluoro-$C_{1-6}$ alkyl-S—, $C_{1-6}$ alkyl-$SO_2$—, $C_{3-6}$ cycloalkyl-$SO_2$—, perfluoro-$C_{1-6}$ alkyl-$SO_2$—, $C_{1-6}$ alkoxy-$C_{1-6}$ alkyl-$SO_2$—, $C_{1-6}$ alkyl-S(O)—, and —$SO_2NH_2$;
$R^3$ is selected from $C_{3-7}$ cycloalkyl and $C_{2-4}$ alkyl;
ring A is a mono-substituted or a di-substituted 5-6 membered heteroaromatic ring consisting of, in addition to the C=N shown, carbon atoms and 0-2 heteroatoms selected from $S(O)_p$, O, and N;
p is selected from 0, 1, and 2;
when ring A is mono-substituted; the substituent is selected from: —CHO; —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_n$—$C(O)R^7$; —$(CH_2)_n$—$OC(O)R^7$; —$(CH_2)_n$—S$(O)_pR^7$; —$(CH_2)_n$—$S(O)_p$—$(CH_2)_n$—$C_{3-8}$ cycloalkyl; —$(CH_2)_n$—$S(O)_p$—$(CH_2)_n$-aryl; —$(CH_2)_n$—$S(O)_p$—$(CH_2)_n$-5-10 membered heterocycle consisting of carbon atoms and 1-3 heteroatoms selected from $S(O)_p$, O, and N; —$(CH_2)_n$—$S(O)_p$—$(CH_2)_n$-5-10 membered heteroaryl consisting of carbon atoms and 1-3 heteroatoms selected from $S(O)_p$, O, and N; —$(CH_2)_n$—$S(O)_p$—$(CH_2)_n$—$NR^{10}R^{11}$; —$(CH_2)_n$—$S(O)_p$—$(CH_2)_n$—$C(O)NR^{10}R^{11}$; —$(CH_2)_n$—S$(O)_p$—$(CH_2)_n$—$C(O)OR^7$; —$(CH_2)_n$—$S(O)_p$—$(CH_2)_n$—C(O)OH; —O—$(CH_2)_n$—$C_{3-8}$ cycloalkyl; —O—$(CH_2)_n$-aryl; —O—$(CH_2)_n$-5-10 membered heterocycle consisting of carbon atoms and 1-3 heteroatoms selected from $S(O)_p$, O, and N; —O—$(CH_2)_n$-5-10 membered heteroaryl consisting of carbon atoms and 1-3 heteroatoms selected from $S(O)_p$, O, and N; —$S(O)_2$—$NR^{10}R^{11}$; —$NR^8R^9$; and —$NHC(O)R^7$; wherein each of these substituents is substituted with 0-2 $R^{12}$ and provided that $R^8$ and $R^9$ cannot both be H;
when ring A is di-substituted; the substituent is selected from: Cl; F; Br; I; —CN; —$NO_2$; $CF_3$; —SCN; —CHO; $C_{1-8}$ alkyl; —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_n$—$S(O)_p$—$(CH_2)_n$—$NR^{10}R^{11}$; —$(CH_2)_n$—$S(O)_p$—$(CH_2)_n$—$C(O)NR^{10}R^{11}$; —$(CH_2)_n$—$S(O)_p$—$(CH_2)_n$—$C(O)OR^7$; —$(CH_2)_n$—$S(O)_p$—$(CH_2)_n$—C(O)OH; —$(CH_2)_n$—C(O)$R^7$; —$(CH_2)_n$—$C(O)OR^7$; —$(CH_2)_n$—C(O)OH; —$(CH_2)_n$—$OC(O)R^7$; —$(CH_2)_n$—$S(O)_pR^7$; —$(CH_2)_n$—$S(O)_p$—$(CH_2)_n$—$C_{3-8}$ cycloalkyl; —$(CH_2)_n$—$S(O)_p$—$(CH_2)_n$-aryl; —$(CH_2)_n$—$S(O)_p$—$(CH_2)_n$-5-10 membered heterocycle consisting of carbon atoms and 1-3 heteroatoms selected from $S(O)_p$, O, and N; —$(CH_2)_n$—$S(O)_p$—$(CH_2)_n$-5-10 membered heteroaryl consisting of carbon atoms and 1-3 heteroatoms selected from $S(O)_p$, O, and N; —$(CH_2)_n$—OH; —$(CH_2)_n$—$OR^7$; —O—$(CH_2)_n$—$C_{3-8}$ cycloalkyl; —O—$(CH_2)_n$-aryl; —O—$(CH_2)_n$-heterocyclyl; —O—$(CH_2)_n$-5-10 membered heteroaryl consisting of carbon atoms and 1-3 heteroatoms selected from $S(O)_p$, O, and N; —$S(O)_2$—$NR^{10}R^{11}$; —$(CH_2)_n$—$NR^8R^9$; and —$NHC(O)R^7$; wherein each of these substituents is substituted with 0-2 $R^{12}$;
n, at each occurrence, is independently selected from 0, 1, 2, 3, 4, 5, and 6;
$R^5$, at each occurrence, is independently selected from H, $C_{1-6}$ alkyl, and perfluoro-$C_{1-6}$ alkyl;
$R^6$, at each occurrence, is independently $C_{1-6}$ alkyl;
$R^7$, at each occurrence, is independently selected from $C_{1-8}$ alkyl and $C_{3-8}$ cycloalkyl;
$R^8$, at each occurrence, is independently selected from H, $C_{1-8}$ alkyl, —$(CH_2)_n$—OH, —$(CH_2)_n$—C(O)OH, aryl, and 5-10 membered heteroaryl consisting of carbon atoms and 1-3 heteroatoms selected from $S(O)_p$, O, and N;
$R^9$, at each occurrence, is independently selected from H, $C_{1-8}$ alkyl, —$(CH_2)_n$—OH, —$(CH_2)_n$—C(O)OH, aryl, and 5-10 membered heteroaryl consisting of carbon atoms and 1-3 heteroatoms selected from $S(O)_p$, O, and N;
alternatively, $R^8$ and $R^9$, together with the nitrogen to which they are attached form a 5-6 membered heterocycle, consisting of, in addition to the nitrogen atom to which $R^8$ and $R^9$ are attached, carbon atoms and 0-2 heteroatoms selected from $S(O)_p$, O, and N;
$R^{10}$, at each occurrence, is independently selected from H; $C_{1-6}$ alkyl; —$(CH_2)_n$—OH; —$(CH_2)_n$—C(O)OH; —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_n$—$NHR^7$; and —$(CH_2)_n$—$NR^7R^7$;

$R^{11}$, at each occurrence, is independently selected from H; $C_{1-6}$ alkyl; —$(CH_2)_n$—OH; —$(CH_2)_n$—C(O)OH; —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_n$—NHR$^7$; and —$(CH_2)_n$—NR$^7$R$^7$;

alternatively, $R^{10}$ and $R^{11}$, together with the nitrogen to which they are attached form a 5-6 membered heterocycle, consisting of, in addition to the nitrogen atom to which $R^{10}$ and $R^{11}$ are attached, carbon atoms and 0-2 heteroatoms selected from $S(O)_p$, O, and N;

$R^{12}$, at each occurrence, is independently selected from $C_{1-6}$ alkyl, Cl, F, Br, I, NO$_2$, —CN, —$(CH_2)_n$—OH, —$(CH_2)_n$—C(O)OH, —$(CH_2)_n$—C(O)OR, NR$^8$R$^9$, NHS(O)$_2$CH$_3$, S(O)$_2$CH$_3$, and S(O)$_2$NH$_2$;

$R^{13}$, at each occurrence, is independently selected from H and $C_{1-4}$ alkyl; and, $R^{14}$, at each occurrence, is independently selected from H and $C_{1-4}$ alkyl.

In another embodiment, the present invention provides a novel compound wherein ring A is mono-substituted and the substituent is selected from: —$(CH_2)_n$—S(O)$_p$—$(CH_2)_{1-4}$—C(O)OR$^7$; —$(CH_2)_n$—S(O)$_p$—$(CH_2)_{1-4}$—C(O)OH; —$(CH_2)_n$—S(O)$_p$—$(CH_2)_{1-4}$—C(O)NR$^{10}$R$^{11}$; and —$(CH_2)_n$-5-6 membered heterocycle consisting of carbon atoms and 1-3 heteroatoms selected from $S(O)_p$, O, and N and is substituted with 0-1 $C_{1-4}$ alkyl; and, $R^7$, at each occurrence, is independently selected from $C_{1-4}$ alkyl and $C_{3-6}$ cycloalkyl.

In another embodiment, the present invention provides a novel compound wherein ring A is di-substituted, the substituent is selected from: Cl; CF$_3$; $C_{1-4}$ alkyl; —$(CH_2)_n$—C(O)OR$^7$; —$(CH_2)_n$—C(O)OH; —$(CH_2)_n$—S(O)$_p$—$(CH_2)_n$—C(O)NR$^{10}$R$^{11}$; and —$(CH_2)_n$—S(O)$_p$—$(CH_2)_n$-5-6 membered heterocycle consisting of carbon atoms and 1-3 heteroatoms selected from $S(O)_p$, O, and N and is substituted with 0-1 $C_{1-4}$ alkyl; and, $R^7$, at each occurrence, is independently selected from $C_{1-4}$ alkyl and $C_{3-6}$ cycloalkyl.

In another embodiment, the present invention provides a novel compound wherein $R^8$ and $R^9$, together with the nitrogen to which they are attached form a heterocycle selected from: piperazine, homopiperazine, and morpholine.

In another embodiment, the present invention provides a novel compound wherein $R^{10}$ and $R^{11}$, together with the nitrogen to which they are attached form a heterocycle selected from: piperidine, piperazine, homopiperazine, pyrrolidine, and morpholine.

In another embodiment, the present invention provides a novel compound wherein the asymmetric carbon shown is in the R configuration.

In another embodiment, the present invention provides a novel compound wherein $R^3$ is selected from $C_{3-5}$ cycloalkyl.

In another embodiment, the present invention provides a novel compound wherein $R^3$ is cyclopentyl.

In another embodiment, the present invention provides a novel compound wherein ring A is thiazole.

In another embodiment, the present invention provides a novel compound wherein
  $R^1$ is selected from H, Cl, F, Br, I, perfluoro-$C_{1-6}$ alkyl, NO$_2$, NH$_2$, $C_{1-6}$ alkyl-SO$_2$—, and —SO$_2$NR$^{13}$R$^{14}$; and,
  $R^2$ is selected from H, Cl, F, Br, I, perfluoro-$C_{1-6}$ alkyl, NO$_2$, NH$_2$, $C_{1-6}$ alkyl-SO$_2$—, and —SO$_2$NR$^{13}$R$^{14}$.

In another embodiment, the present invention provides a novel compound wherein $R^2$ is $C_{1-6}$ alkyl-SO$_2$—.

In another embodiment, the present invention provides a novel compound wherein $R^1$ and $R^2$ are both Cl.

In another embodiment, the present invention provides a novel compound wherein $R^1$ is H and $R^2$ is $C_{1-6}$ alkyl-SO$_2$—.

In another embodiment, the present invention provides a novel compound wherein $R^1$ is selected from $C_1$, CF$_3$, and CH$_3$ and $R^2$ is $C_{1-6}$ alkyl-SO$_2$—.

In another embodiment, the present invention provides a novel compound wherein $R^1$ is H and $R^2$ is CH$_3$—SO$_2$—.

In another embodiment, the present invention provides a novel compound wherein the compound is selected from:
{2-[3-Cyclopentyl-2-(4-methanesulfonyl-phenyl)-propionylamino]-5-methyl-thiazol-4-yl}-acetic acid ethyl ester;
3-Cyclopentyl-2-(4-methanesulfonyl-phenyl)-N-[4-methyl-5-(4-methyl-piperazine-1-sulfonyl)-thiazol-2-yl]-propionamide;
3-Cyclopentyl-2-(4-methanesulfonyl-phenyl)-N-[5-(4-methyl-piperazin-1-yl)thiazol-2-yl]-propionamide;
{2-[3-Cyclopentyl-2-(4-methanesulfonyl-phenyl)-propionylamino]-thiazol-5-ylsulfanyl}-acetic acid ethyl ester;
{5-Chloro-2-[3-cyclopentyl-2-(4-methanesulfonyl-phenyl)-propionylamino]-thiazol-4-yl}-acetic acid ethyl ester;
{2-[3-Cyclopentyl-2-(4-methanesulfonyl-phenyl)-propionylamino]-5-methyl-thiazol-4-yl}-acetic acid;
{2-[3-Cyclopentyl-2-(4-methanesulfonyl-phenyl)-propionylamino]-thiazol-5-ylsulfanyl}-acetic acid;
{5-Chloro-2-[3-cyclopentyl-2-(4-methanesulfonyl-phenyl)-propionylamino]-thiazol-4-yl}-acetic acid;
3-Cyclopentyl-N-[5-(2-diethylaminoethylsulfanyl)thiazol-2-yl]-2-(4-methanesulfonylphenyl)propionamide; and,
3-Cyclopentyl-N-[5-(methylsulfanyl)thiazol-2-yl]-2-(4-methanesulfonylphenyl)propionamide;
or a pharmaceutically acceptable salt thereof.

In another embodiment, the present invention provides a novel compound wherein the compound is selected from:
(R)-{2-[3-Cyclopentyl-2-(4-methanesulfonyl-phenyl)-propionylamino]-5-methyl-thiazol-4-yl}-acetic acid ethyl ester;
(R)-3-Cyclopentyl-2-(4-methanesulfonyl-phenyl)-N-[4-methyl-5-(4-methyl-piperazine-1-sulfonyl)-thiazol-2-yl]-propionamide;
(R)-3-Cyclopentyl-2-(4-methanesulfonyl-phenyl)-N-[5-(4-methyl-piperazin-1-yl)-thiazol-2-yl]-propionamide;
(R)-{2-[3-Cyclopentyl-2-(4-methanesulfonyl-phenyl)-propionylamino]-thiazol-5-ylsulfanyl}-acetic acid ethyl ester;
(R)-{5-Chloro-2-[3-cyclopentyl-2-(4-methanesulfonyl-phenyl)propionylamino]-thiazol-4-yl}-acetic acid ethyl ester;
(R)-{2-[3-Cyclopentyl-2-(4-methanesulfonyl-phenyl)-propionylamino]-5-methyl-thiazol-4-yl}-acetic acid;
(R)-{2-[3-Cyclopentyl-2-(4-methanesulfonyl-phenyl)-propionylamino]-thiazol-5-ylsulfanyl}-acetic acid;
(R)-{5-Chloro-2-[3-cyclopentyl-2-(4-methanesulfonyl-phenyl)propionylamino]-thiazol-4-yl}-acetic acid;
(R)-3-cyclopentyl-N-[5-(2-diethylaminoethylsulfanyl)thiazol-2-yl]-2-(4-methanesulfonylphenyl)propionamide; and,
(R)-3-cyclopentyl-N-[5-(methylsulfanyl)thiazol-2-yl]-2-(4-methanesulfonylphenyl)propionamide;
or a pharmaceutically acceptable salt thereof.

In another embodiment, the present invention provides a novel pharmaceutical composition, comprising: a pharmaceutically acceptable carrier and a compound of the present invention or a pharmaceutically acceptable salt thereof.

In another embodiment, the present invention provides a novel method of treating type II diabetes, comprising: administering to a subject in need thereof a therapeutically effective amount of a compound of the present invention.

In another embodiment, the present invention provides a novel method of treating a condition or disorder, comprising: administering to a subject in need thereof a therapeutically effective amount of a compound of the present invention, wherein the condition or disorder is selected from a metabolic disorder, blood glucose lowering, hyperglycemia, impaired glucose tolerance (IGT), Syndrome X, Polycystic Ovarian Syndrome, impaired fasting glucose (IFG), type I diabetes, delaying the progression of impaired glucose tolerance (IGT) to type II diabetes, delaying the progression of non-insulin requiring type II diabetes to insulin requiring type II diabetes, dyslipidemia, hyperlipidemia, hypertension, treatment or prophylaxis of obesity, lowering of food intake, appetite regulation, regulating feeding behaviour, and enhancing the secretion of enteroincretins.

In another aspect the invention provides a compound of formula I:

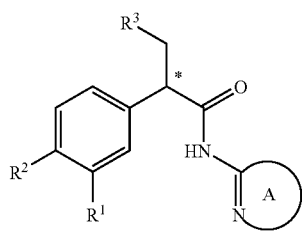

I wherein, the * indicates an asymmetric atom;

$R^1$ is selected from H, Cl, F, Br, I, $NH_2$, —NHOH, —CN, —$NO_2$, $C_{1-6}$ alkyl, —$OR^5$, —C(O)$OR^6$, perfluoro-$C_{1-6}$ alkyl, $C_{1-6}$ alkyl-S—, perfluoro-$C_{1-6}$ alkyl-S—, $C_{1-6}$ alkyl-$SO_2$—, perfluoro-$C_{1-6}$ alkyl-$SO_2$—, $C_{1-6}$ alkoxy-$C_{1-6}$ alkyl-$SO_2$—, $C_{1-6}$ alkyl-S(O)—, and —$SO_2NR^{13}R^{14}$;

$R^2$ is selected from H, Cl, F, Br, I, $NH_2$, —NHOH, —CN, —$NO_2$, $C_{1-6}$ alkyl, —$OR^5$, —O(O)$OR^6$, perfluoro-$C_{1-6}$ alkyl, $C_{1-6}$ alkyl-S—, perfluoro-$C_{1-6}$ alkyl-S—, $C_{1-6}$ alkyl-$SO_2$—, $C_{3-6}$ cycloalkyl-$SO_2$—, perfluoro-$C_{1-6}$ alkyl-$SO_2$—, $C_{1-6}$ alkoxy-$C_{1-6}$ alkyl-$SO_2$—, $C_{1-6}$ alkyl-S(O)—, and —$SO_2NH_2$;

$R^3$ is selected from $C_{3-7}$ cycloalkyl and $C_{2-4}$ alkyl;

ring A is a mono-substituted or a di-substituted 5-6 membered heteroaromatic ring consisting of, in addition to the C=N shown, carbon atoms and 0-2 heteroatoms selected from $S(O)_p$, O, and N;

when ring A is mono-substituted; the substituent is selected from: —CHO; —SCN, —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_n$—C(O)$R^7$; —$(CH_2)_n$—OC(O)$R^7$; —$(CH_2)_n$—S(O)$_pR^7$; —$(CH_2)_m$—S(O)$_p$—$(CH_2)_n$—$C_{3-8}$ cycloalkyl; —$(CH_2)_m$—S(O)$_p$—$(CH_2)_n$-aryl; —$(CH_2)_m$—S(O)$_p$—$(CH_2)_n$-5-10 membered heterocycle consisting of carbon atoms and 1-3 heteroatoms selected from $S(O)_p$, O, and N; —$(CH_2)_m$—S(O)$_p$—$(CH_2)_n$-5-10 membered heteroaryl consisting of carbon atoms and 1-3 heteroatoms selected from $S(O)_p$, O, and N; —$(CH_2)_m$—S(O)$_p$—$(CH_2)_n$—$NR^{10}R^{11}$; —$(CH_2)_m$—S(O)$_p$—$(CH_2)_n$—C(O)$NR^{10}R^{11}$; —$(CH_2)_m$—S(O)$_p$—$(CH_2)_n$—C(O)$OR^7$; —$(CH_2)_m$—S(O)$_p$—$(CH_2)_n$—C(O)OH; —O—$(CH_2)_n$—$C_{3-8}$ cycloalkyl; —O—$(CH_2)_n$-aryl; —O—$(CH_2)_n$-5-10 membered heterocycle consisting of carbon atoms and 1-3 heteroatoms selected from $S(O)_p$, O, and N; —O—$(CH_2)_n$-5-10 membered heteroaryl consisting of carbon atoms and 1-3 heteroatoms selected from $S(O)_p$, O, and N; —S(O)$_p$—$(CH_2)_n$—, —$SO_2$—$NR^{10}R^{11}$; —$NR^8R^9$; and —NHC(O)$R^7$; wherein each of these substituents is substituted with 0-2 $R^{12}$ and provided that $R^8$ and $R^9$ cannot both be H;

when ring A is di-substituted; the substituent is selected from: Cl; F; Br; I; —CN; —$NO_2$; $CF_3$; —SCN; —CHO; $C_{1-8}$ alkyl; —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_m$—S(O)$_p$—$(CH_2)_n$—$NR^{10}R^{11}$; —$(CH_2)_m$—S(O)$_p$—$(CH_2)_n$—C(O)$NR^{10}R^{11}$; —$(CH_2)_m$—S(O)$_p$—$(CH_2)_n$—C(O)$OR^7$; —$(CH_2)_m$—S(O)$_p$—$(CH_2)_n$—C(O)OH; —$(CH_2)_n$—C(O)$R^7$; —$(CH_2)_n$—C(O)$OR^7$; —$(CH_2)_n$—C(O)OH; —$(CH_2)_n$—OC(O)$R^7$; —$(CH_2)_n$—S(O)$_pR^7$; —$(CH_2)_m$—S(O)$_p$—$(CH_2)_n$—$C_{3-8}$ cycloalkyl; —$(CH_2)_m$—S(O)$_p$—$(CH_2)_n$-aryl; —$(CH_2)_m$—S(O)$_p$—$(CH_2)_n$-5-10 membered heterocycle consisting of carbon atoms and 1-3 heteroatoms selected from $S(O)_p$, O, and N; —$(CH_2)_m$—S(O)$_p$—$(CH_2)_n$-5-10 membered heteroaryl consisting of carbon atoms and 1-3 heteroatoms selected from $S(O)_p$, O, and N; —$(CH_2)_n$—OH; —$(CH_2)_n$—$OR^7$; —O—$(CH_2)_n$—$C_{3-8}$ cycloalkyl; —O—$(CH_2)_n$-aryl; —O—$(CH_2)_n$-heterocyclyl; —O—$(CH_2)_n$-5-10 membered heteroaryl consisting of carbon atoms and 1-3 heteroatoms selected from $S(O)_p$, O, and N; —S(O)$_2$—$NR^{10}R^{11}$; —$(CH_2)_n$—$NR^8R^9$; and —NHC(O)$R^7$; wherein each of these substituents is substituted with 0-2 $R^{12}$;

$R^5$, at each occurrence, is independently selected from H, $C_{1-6}$ alkyl, and perfluoro-$C_{1-6}$ alkyl;

$R^6$, at each occurrence, is independently $C_{1-6}$ alkyl;

$R^7$, at each occurrence, is independently selected from $C_{1-8}$ alkyl and $C_{3-8}$ cycloalkyl;

$R^8$, at each occurrence, is independently selected from H, $C_{1-8}$ alkyl, —$(CH_2)_n$—OH, —$(CH_2)_n$—C(O)OH, aryl, and 5-10 membered heteroaryl consisting of carbon atoms and 1-3 heteroatoms selected from $S(O)_p$, O, and N;

$R^9$, at each occurrence, is independently selected from H, $C_{1-8}$ alkyl, —$(CH_2)_n$—OH, —$(CH_2)_n$—C(O)OH, aryl, and 5-10 membered heteroaryl consisting of carbon atoms and 1-3 heteroatoms selected from $S(O)_p$, O, and N;

alternatively, $R^8$ and $R^9$, together with the nitrogen to which they are attached form a 5-6 membered heterocycle, consisting of, in addition to the nitrogen atom to which $R^8$ and $R^9$ are attached, carbon atoms and 0-2 heteroatoms selected from $S(O)_p$, O, and N;

$R^{10}$, at each occurrence, is independently selected from H; $C_{1-6}$ alkyl; —$(CH_2)_n$—OH; —$(CH_2)_n$—C(O)OH; —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_n$—$NHR^7$; and —$(CH_2)_n$—$NR^7R^7$;

$R^{11}$, at each occurrence, is independently selected from H; $C_{1-6}$ alkyl; —$(CH_2)_n$—OH; —$(CH_2)_n$—C(O)OH; —$(CH_2)_n$—$C_{3-8}$ cycloalkyl; —$(CH_2)_n$-aryl; —$(CH_2)_n$-5-10 membered heterocycle consisting of carbon atoms and 1-3 heteroatoms selected from $S(O)_p$, O, and N; —$(CH_2)_n$-5-10 membered heteroaryl consisting of carbon atoms and 1-3 heteroatoms selected from $S(O)_p$, O, and N; —$(CH_2)_n$—$NHR^7$; and —$(CH_2)_n$—$NR^7R^7$;

alternatively, $R^{10}$ and $R^{11}$, together with the nitrogen to which they are attached form a 5-6 membered heterocycle, consisting of, in addition to the nitrogen atom to which $R^{10}$ and $R^{11}$ are attached, carbon atoms and 0-2 heteroatoms selected from $S(O)_p$, O, and N; and wherein the heterocycle thus formed is substituted with 0-2 $R^{12}$;

$R^{12}$, at each occurrence, is independently selected from $C_{1-6}$ alkyl, Cl, F, Br, I, $NO_2$, —CN, —$(CH_2)_n$—OH, —$(CH_2)_n$—C(O)OH, —$(CH_2)_n$—C(O)OR, $NR^8R^9$, NHS$(O)_2CH_3$, $S(O)_2CH_3$, and $S(O)_2NH_2$;

$R^{13}$, at each occurrence, is independently selected from H and $C_{1-4}$ alkyl;

$R^{14}$, at each occurrence, is independently selected from H and $C_{1-4}$ alkyl;

p, at each occurrence, is selected from 0, 1, and 2;

n, at each occurrence, is independently selected from 0, 1, 2, 3, 4, 5, and 6; and m, at each occurrence, is independently selected from 0, 1, and 2.

In one embodiment hereof ring A is mono-substituted and the substituent is selected from: —$(CH_2)_{0-2}$—$S(O)_p$—$(CH_2)_{1-4}$—$C(O)OR^7$; —$(CH_2)_{0-2}$—$S(O)_p$—$(CH_2)_{1-4}$—C(O)OH; —$(CH_2)_{0-2}$—$S(O)_p$—$(CH_2)_n$—$NR^{10}R^{11}$; —$(CH_2)_{0-2}$—$S(O)_p$—$(CH_2)_n$—$C(O)NR^{10}R^{11}$; and —$(CH_2)_n$-5-6 membered heterocycle consisting of carbon atoms and 1-3 heteroatoms selected from $S(O)_p$, O, and N and is substituted with 0-1 $C_{1-4}$ alkyl; and, $R^7$, at each occurrence, is independently selected from $C_{1-4}$ alkyl and $C_{3-6}$ cycloalkyl.

In another embodiment hereof ring A is mono-substituted and the substituent is selected from: —$S(O)_2$—$CH_2$—$C(O)OR^7$; —$S(O)_2$—$CH_2$—C(O)OH; —S—$CH_2$—$C(O)OR^7$; —S—$CH_2$—$CH_2$—$C(O)OR^7$; —S—$CH_2$—C(O)OH—S—$CH_2$—$CH_2$—C(O)OH; —S—$(CH_2)_2$—$NR^{10}R^{11}$; —S—$CH_2$—$C(O)NR^{10}R^{11}$; and piperazine; and, $R^7$, at each occurrence, is independently selected from $C_{1-2}$ alkyl.

In another embodiment hereof ring A is di-substituted, the substituent is selected from: Cl; $CF_3$; $C_{1-4}$ alkyl; —$(CH_2)_n$—$C(O)OR^7$; —$(CH_2)_n$—C(O)OH; —$(CH_2)_n$—$S(O)_p$—$(CH_2)_n$—$C(O)NR^{10}R^{11}$; and —$(CH_2)_n$—$S(O)_p$—$(CH_2)_n$-5-6 membered heterocycle consisting of carbon atoms and 1-3 heteroatoms selected from $S(O)_p$, O, and N and is substituted with 0-1 $C_{1-4}$ alkyl; and, $R^7$, at each occurrence, is independently selected from $C_{1-4}$ alkyl and $C_{3-6}$ cycloalkyl.

In another embodiment hereof ring A is di-substituted, the substituent is selected from: Cl; $CH_3$; —$CH_2$—$C(O)OR^7$; —$CH_2$—C(O)OH; and —$S(O)_2$-piperazine optionally substituted with $CH_3$; and, $R^7$, at each occurrence, is independently selected from $C_{1-2}$ alkyl.

In another embodiment hereof m is 0.

In another embodiment hereof n is 1.

In another embodiment hereof n is 2.

In another embodiment hereof $R^8$ and $R^9$, together with the nitrogen to which they are attached form a heterocycle selected from: piperazine, homopiperazine, and morpholine.

In another embodiment hereof $R^{10}$ and $R^{11}$, together with the nitrogen to which they are attached form a heterocycle selected from: piperidine, piperazine, homopiperazine, pyrrolidine, and morpholine.

In another embodiment hereof the asymmetric carbon shown is in the R configuration.

In another embodiment hereof $R^3$ is selected from $C_{3-5}$ cycloalkyl.

In another embodiment hereof $R^3$ is cyclopentyl.

In another embodiment hereof ring A is thiazole.

In another embodiment hereof $R^1$ is selected from H, Cl, F, Br, I, perfluoro-$C_{1-6}$ alkyl, $NO_2$, $NH_2$, $C_{1-6}$ alkyl-$SO_2$—, and —$SO_2NR^{13}R^{14}$; and, $R^2$ is selected from H, Cl, F, Br, I, perfluoro-$C_{1-6}$ alkyl, $NO_2$, $NH_2$, $C_{1-6}$ alkyl-$SO_2$—, and —$SO_2NR^{13}R^{14}$.

In another embodiment hereof $R^2$ is $C_{1-6}$ alkyl-$SO_2$—.

In another embodiment hereof $R^1$ and $R^2$ are both Cl.

In another embodiment hereof $R^1$ is H and $R^2$ is $C_{1-6}$ alkyl-$SO_2$—.

In another embodiment hereof $R^1$ is selected from $C_1$, $CF_3$, and $CH_3$ and $R^2$ is $C_{1-6}$ alkyl-$SO_2$—.

In another embodiment hereof $R^1$ is H and $R^2$ is $CH_3$—$SO_2$—.

In another embodiment hereof the compound is selected from:

{2-[3-Cyclopentyl-2-(4-methanesulfonyl-phenyl)-propionylamino]-5-methyl-thiazol-4-yl}-acetic acid ethyl ester 3-Cyclopentyl-2-(4-methanesulfonyl-phenyl)-N-[4-methyl-5-(4-methyl-piperazine-1-sulfonyl)-thiazol-2-yl]-propionamide 3-Cyclopentyl-2-(4-methanesulfonyl-phenyl)-N-[5-(4-methyl-piperazin-1-yl)-thiazol-2-yl]-propionamide {2-[3-Cyclopentyl-2-(4-methanesulfonyl-phenyl)-propionylamino]-thiazol-5-ylsulfanyl}-acetic acid ethyl ester {5-Chloro-2-[3-cyclopentyl-2-(4-methanesulfonyl-phenyl)-propionylamino]-thiazol-4-yl}-acetic acid ethyl ester {2-[3-Cyclopentyl-2-(4-methanesulfonyl-phenyl)-propionylamino]-5-methyl-thiazol-4-yl}-acetic acid {2-[3-Cyclopentyl-2-(4-methanesulfonyl-phenyl)propionylamino]-thiazol-5-ylsulfanyl}-acetic acid {5-Chloro-2-[3-cyclopentyl-2-(4-methanesulfonyl-phenyl)-propionylamino]-thiazol-4-yl}-acetic acid (R)-3-Cyclopentyl-2-(4-methanesulfonyl-phenyl)-N-(5-thiocyanato-thiazol-2-yl)propionamide (R)-3-Cyclopentyl-N-[5-(2-diethylamino-ethylsulfanyl)-thiazol-2-yl]-2-(4-methanesulfonyl-phenyl)-propionamide (R)-3-Cyclopentyl-2-(4-methanesulfonyl-phenyl)-N-(5-methylsulfanyl-thiazol-2-yl)propionamide 3-Cyclopentyl-N-(5-diethylcarbamoylmethylsulfanyl-thiazol-2-yl)-2-(4-methanesulfonyl-phenyl)-propionamide {2-[3-Cyclopentyl-2-(4-methanesulfonyl-phenyl)-propionylamino]-thiazole-5-sulfonyl}-acetic acid (R)-{2-[3-Cyclopentyl-2-(4-methanesulfonyl-phenyl)-propionylamino]-thiazol-5-ylsulfanyl}-acetic acid ethyl ester (R)-{2-[3-Cyclopentyl-2-(4-methanesulfonyl-phenyl)-propionylamino]-thiazol-5-ylsulfanyl}-acetic acid (R)-3-{2-[3-Cyclopentyl-2-(4-methanesulfonyl-phenyl)-propionylamino]-thiazol-5-ylsulfanyl}-propionic acid ethyl ester (R)-3-Cyclopentyl-2-(4-methanesulfonyl-phenyl)-N-[5-(2-oxo-2-piperazin-1-ylethylsulfanyl)-thiazol-2-yl]-propionamide (R)-3-Cyclopentyl-2-(4-methanesulfonyl-phenyl)-N-[5-(2-morpholin-4-yl-2-oxoethylsulfanyl)-thiazol-2-yl]-propionamide (R)-3-Cyclopentyl-2-(4-methanesulfonyl-phenyl)-N-{5-[2-(4-methyl-piperazin-1-yl)-2-oxo-ethylsulfanyl]-thiazol-2-yl}-propionamide (R)-3-Cyclopentyl-2-(4-methanesulfonyl-phenyl)-N-[5-(2-oxo-2-piperidin-1-ylethylsulfanyl)-thiazol-2-yl]-propionamide (R)-3-Cyclopentyl-N-[5-(2-dimethylamino-ethylsulfanyl)-thiazol-2-yl]-2-(4-methanesulfonyl-phenyl)-propionamide (R)-3-Cyclopentyl-2-(4-methanesulfonyl-phenyl)-N-[5-(2-morpholin-4-ylethylsulfanyl)-thiazol-2-yl]-propionamide
(R)-3-Cyclopentyl-2-(4-methanesulfonyl-phenyl)-N-[5-(2-piperidin-1-yl-ethylsulfanyl)thiazol-2-yl]-propionamide
(R)-3-{2-[3-Cyclopentyl-2-(4-methanesulfonyl-phenyl)-propionylamino]-thiazol-5-ylsulfanyl}-propionic acid
or a pharmaceutically acceptable salt thereof.

In an additional aspect the invention provides a pharmaceutical composition, comprising: a pharmaceutically acceptable carrier and a compound of the invention or a pharmaceutically acceptable salt thereof.

In an additional aspect the invention provides a method of treating type II diabetes, comprising: administering to a subject in need thereof a therapeutically effective amount of a compound of the invention.

In an additional aspect the invention provides a method of treating a condition or disorder, comprising: administering to a subject in need thereof a therapeutically effective amount of a compound of the invention, wherein the condition or disorder is selected from a metabolic disorder, blood glucose lowering, hyperglycemia, impaired glucose tolerance (IGT), Syndrome X, Polycystic Ovarian Syndrome, impaired fasting glucose (IFG), type I diabetes, delaying the progression of impaired glucose tolerance (IGT) to type II diabetes, delaying the progression of non-insulin requiring type II diabetes to insulin requiring type II diabetes, dyslipidemia, hyperlipidemia, hypertension, treatment or prophylaxis of obesity, lowering of food intake, appetite regulation, regulating feeding behaviour, and enhancing the secretion of enteroincretins.

In the present invention, there is an asymmetric center in the compound of formula I that is represented by an asterisk (*). As a result, compounds of the present invention may be racemic or have the stereochemistry shown in formulae Ia and Ib.

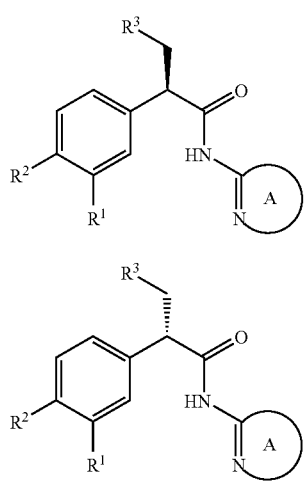

Preferably, the compounds of the present invention are in the R configuration (e.g., formula Ia).

In another embodiment of the present invention, the present compounds are administered in combination with one or more further active substances in any suitable ratios. When used in combination with one or more further active substances, the combination of compounds is preferably a synergistic combination. Synergy occurs when the effect of the compounds when administered in combination is greater than the additive effect of the compounds when administered as a single agent. In general, a synergistic effect is most clearly demonstrated at sub-optimal concentrations of the compounds. Such further active agents may be selected from antidiabetic agents, antihyperlipidemic agents, anti-obesity agents, antihypertensive agents, and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells e.g., potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In another embodiment of the present invention, the present compounds are administered in combination with a sulphonylurea, e.g., tolbutamide, chlorpropamide, tolazamide, glibenclamide, glipizide, glimepiride, glicazide, or glyburide.

In another embodiment of the present invention, the present compounds are administered in combination with a biguanide, e.g., metformin.

In another embodiment of the present invention, the present compounds are administered in combination with a meglitinide, e.g., repaglinide or senaglinide/nateglinide.

In another embodiment of the present invention, the present compounds are administered in combination with a thiazolidinedione insulin sensitizer, e.g., troglitazone, ciglitazone, pioglitazone, rosiglitazone, isaglitazone, darglitazone, englitazone, CS-011/CI-1037, T 174, the compounds disclosed in WO 97/41097 (DRF-2344), WO 97/41119, WO 97/41120, WO 00/41121. and WO 98/45292 (Dr. Reddy's Research Foundation), which are incorporated herein by reference.

In another embodiment of the present invention, the present compounds may be administered in combination with an insulin sensitizer, e.g., GI 262570, YM-440, MCC-555, JTT-501, AR-H039242, KRP-297, GW-409544, CRE-16336, AR-H049020, LY510929, MBX-102, CLX-0940, GW-501516, the compounds disclosed in WO 99/19313 (NN622/DRF-2725), WO 00/50414, WO 00/63191, WO 00/63192, WO 00/63193 (Dr. Reddy's Research Foundation), WO 00/23425, WO 00/23415, WO 00/23451, WO 00/23445, WO 00/23417, WO 00/23416, WO 00/63153, WO 00/63196, WO 00/63209, WO 00/63190, and WO 00/63189 (Novo Nordisk A/S), which are incorporated herein by reference.

In another embodiment of the present invention, the present compounds are administered in combination with an α-glucosidase inhibitor, e.g., voglibose, emiglitate, miglitol, or acarbose.

In another embodiment of the present invention, the present compounds are administered in combination with a glycogen phosphorylase inhibitor, e.g., the compounds described in WO 97/09040 (Novo Nordisk A/S).

In another embodiment of the present invention, the present compounds are administered in combination with an agent acting on the ATP-dependent potassium channel of the pancreatic β-cells, e.g., tolbutamide, glibenclamide, glipizide, glicazide, BTS-67582, or repaglinide.

In another embodiment of the present invention, the present compounds are administered in combination with nateglinide.

In another embodiment of the present invention, the present compounds are administered in combination with an antihyperlipidemic agent or a antilipidemic agent, e.g., cholestyramine, colestipol, clofibrate, gemfibrozil, lovastatin, pravastatin, simvastatin, probucol, or dextrothyroxine.

In another embodiment, the compounds of the present invention may be administered in combination with one or more anti-obesity agents or appetite regulating agents. Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further anti-obesity agents are bupropion (antidepressant), topiramate (anticonvulsant), ecopipam (dopamine D1/D5 antagonist), and naltrexone (opioid antagonist).

In another embodiment of the present invention, the anti-obesity agent is leptin.

In another embodiment of the present invention, the anti-obesity agent is a serotonin and norepinephrine reuptake inhibitor, e.g., sibutramine.

In another embodiment of the present invention, the anti-obesity agent is a lipase inhibitor, e.g., orlistat.

In another embodiment of the present invention, the anti-obesity agent is an adrenergic CNS stimulating agent, e.g., dexamphetamine, amphetamine, phentermine, mazindol phendimetrazine, diethylpropion, fenfluramine, or dexfenfluramine.

In another embodiment of the present invention, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In another embodiment of the present invention, the present compounds are administered in combination with insulin, insulin derivatives or insulin analogues.

In another embodiment of the present invention, the insulin is an insulin derivative is selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl Lys$^{B28}$Pro$^{B29}$ human insulin, B28-$N^\epsilon$-palmitoyl Lys$^{B28}$Pro$^{B29}$ human insulin, B30-$N^\epsilon$-myristoyl-Thr$^{B29}$Lys$^{B30}$ human insulin, B30-$N^\epsilon$-palmitoyl-Thr$^{B29}$Lys$^{B30}$ human insulin, B29-$N^\epsilon$-(N-palmitoyl-γ-glutamyl)des(B30) human insulin, B29-$N^\epsilon$-(N-lithocholyl-γ-glutamyl)-des(B30) human insulin, B29-$N^\epsilon$-(ω-carboxyheptadecanoyl)-des(B30) human insulin and B29-$N^\epsilon$-(ω-carboxyheptadecanoyl) human insulin.

In another embodiment of the present invention, the insulin derivative is B29-$N^\epsilon$-myristoyl-des(B30) human insulin.

In another embodiment of the present invention, the insulin is an acid-stabilised insulin. The acid-stabilised insulin may be selected from analogues of human insulin having one of the following amino acid residue substitutions:

A21G
A21G, B28K, B29P
A21G, B28D
A21G, B28E
A21G, B3K, B29E
A21G, desB27
A21G, B9E
A21G, B9D
A21G, B10E insulin.

In another embodiment of the present invention, the insulin is an insulin analogue. The insulin analogue may be selected from the group consisting of: an analogue wherein position B28 is Asp, Lys, Leu, Val, or Ala and position B29 is Lys or Pro; des(B28-B30); des(B27); or, des(B30) human insulin.

In another embodiment the analogue is an analogue of human insulin wherein position B28 is Asp or Lys, and position B29 is Lys or Pro.

In another embodiment the analogue is des(B30) human insulin.

In another embodiment the insulin analogue is an analogue of human insulin wherein position B28 is Asp.

In another embodiment the analogue is an analogue wherein position B3 is Lys and position B29 is Glu or Asp.

In another embodiment the GLP-1 derivative to be employed in combination with a compound of the present invention refers to GLP-1 (1-37), exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1 (1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1 (7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1(1-37) are e.g. Met$^8$-GLP-1(7-37) wherein the alanine in position 8 has been replaced by methionine and the amino acid residues in position 1 to 6 have been deleted, and Arg$^{34}$-GLP-1(7-37) wherein the valine in position 34 has been replaced with arginine and the amino acid residues in position 1 to 6 have been deleted. An example of an insulinotropic analogue of exendin-4(1-39) is Ser$^2$Asp$^3$-exendin-4 (1-39) wherein the amino acid residues in position 2 and 3 have been replaced with serine and aspartic acid, respectively (this particular analogue also being known in the art as exendin-3). Insulinotropic derivatives of GLP-1(1-37), exendin-4 (1-39) and analogues thereof are what the person skilled in the art considers to be derivatives of these peptides, i.e., having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogues thereof are GLP-1(7-36)-amide, Arg$^{34}$, Lys$^{26}$(N$^\epsilon$-(γ-Glu(N$^\alpha$-hexadecanoyl)))-GLP-1(7-37) and Tyr$^{31}$-exendin-4 (1-31)-amide. Further examples of GLP-1(1-37), exendin-4 (1-39), insulinotropic fragments thereof, insulinotropic analogues thereof and insulinotropic derivatives thereof are described in WO 98/08871, WO 99/43706, U.S. Pat. No. 5,424,286, and WO 00/09666.

In another embodiment of the present invention, the present compounds are administered in combination with more than one of the above-mentioned compounds, e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In another embodiment of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous, and intradermal) route, the oral route being preferred. the preferred route will depend on the general condition and age of the subject to be treated, the nature of the condition to be treated, and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art. Liquid dosage forms for oral administration include solutions, emulsions, aqueous or oily suspensions, syrups, and elixirs. Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the pre-sent invention. Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day, such as 1 to 3 times per day, may contain from 0.05 to about 1000 mg, preferably from about 0.1 to about 500 mg, and more preferably from about 0.5 mg to about 200 mg.

For parenteral routes such as intravenous, intrathecal, intramuscular, and similar administration, typically doses are in the order of about half the dose employed for oral administration.

The compounds of this invention are generally utilized as the free sub-stance or as a pharmaceutically acceptable salt thereof. Examples are an acid addition salt of a compound having the utility of a free base and a base addition salt of a compound having the utility of a free acid. The term "pharmaceutically acceptable salt(s)" refers to non-toxic salts of the compounds of this invention which are generally prepared by reacting the free base with a suitable organic or inorganic acid or by reacting the free acid with a suitable organic or inorganic base. When a compound according to the present invention contains a free base, such salts are prepared in a conventional manner by treating a solution or suspension of the compound with a chemical equivalent of a pharmaceutically acceptable acid. When a compound according to the present invention contains a free acid, such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation, such as sodium or ammonium ion. Other salts which are not pharmaceutically acceptable may be useful in the preparation of compounds of the present invention and these form a further aspect of the present invention.

Representative examples of suitable inorganic acids include hydrochloric, hydrobromic, hydroiodic, phosphoric, sulfuric, nitric acids, and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, and the like. Further examples of pharmaceutically acceptable inorganic or organic acid addition salts include the pharmaceutically acceptable salts listed in J. Pharm. Sci. 1977, 66, 2. Examples of metal salts include lithium, sodium, potassium, magnesium salts, and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts, and the like.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further embodiment, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |

| Coating: | | |
|---|---|---|
| Hydroxypropyl methylcellulose | approx. | 9 mg |
| Mywacett 9-40 T** | approx. | 0.9 mg |
| Polacrillin potassium NF, tablet disintegrant, Rohm and Haas. | | |

**Acylated monoglyceride used as plasticizer for film coating.

If desired, the pharmaceutical composition of the present invention may comprise a compound according to the present invention in combination with further active substances such as those described in the foregoing.

Definitions

As used herein, "substituted" signifies that one or more hydrogen atoms are replaced by the designated substituent. Only pharmaceutically stable compounds are intended to be covered.

The present invention includes all isotopes of atoms occurring in the pre-sent compounds. Isotopes include those atoms having the same atomic number but different mass numbers. By way of general example and without limitation, isotopes of hydrogen include tritium and deuterium. Isotopes of carbon include C-13 and C-14.

As used herein, "alkyl" includes both straight chain and branched alkyl groups having the designated number of carbon atoms (e.g., 1, 2, 3, 4, 5, 6, 7, or 8). Examples of alkyl groups include, but are not limited to, methyl, ethyl, n-propyl, i-propyl, n-butyl, i-butyl, s-butyl, and t-butyl. Preferred alkyl groups are methyl and ethyl.

As used herein, "perfluoro-alkyl" means an alkyl group as defined above wherein all of the hydrogens of the alkyl group are replaced by fluoro. Preferred perfluoro-alkyl groups include, but are not limited to, trifluoromethyl, pentafluoroethyl, and heptafluoropropyl.

As used herein, "alkoxy" signifies a lower alkyl group as defined above linked via an oxygen to the remainder of the molecule and includes both straight chain and branched chain alkyl groups having the designated number of carbon atoms. Examples of alkoxy include, but are not limited to, methoxy, ethoxy, n-propoxy, i-propoxy, n-butoxy, i-butoxy, s-butoxy, and t-butoxy. Preferred alkoxy groups are methoxy and ethoxy. As used herein, "alkoxy-alkyl" signifies an alkyl group linked via an oxygen to another alkyl group, which is linked to the remainder of the molecule.

As used herein, "cycloalkyl" means a ring having the number of designated carbon atoms and having only single bonds between the carbon atoms. Examples of cycloalkyl include, but are not limited to cyclopropyl, cyclobutyl, cyclopentyl, cyclohexyl, and cycloheptyl. A preferred cycloalkyl group is cyclopentyl.

As used herein, "aryl" signifies a mononuclear or polynuclear aromatic hydrocarbon such as phenyl, biphenyl, indene, fluorene, naphthyl (1-naphthyl, 2-naphthyl), anthracene (1-anthracenyl, 2-anthracenyl, 3-anthracenyl), and phenantnthryl, depending on the number of carbon atoms designated.

Heteroaromatic ring A is A five- or six-membered heteroaromatic ring having the shown nitrogen atom and from 0 to 2 additional heteroatoms selected from the group consisting of oxygen, nitrogen, or sulfur and connected by a ring carbon to the amine of the amide group shown. If sulphur is present, then it can be mono- or di-oxidized. If a second nitrogen is present, then it can be N, NH, or substituted N. Heteroaromatic rings include, but are not limited to, pyrazinyl, pyrimidinyl, pyridazinyl, triazinyl, thiazolyl, thiadiazolyl, oxazolyl, isoxazolyl, isothiazolyl, imidazolyl, and pyrazolyl. The ring carbon atom of the heteroaromatic ring which is connected via the amide linkage to form the compound of formula I cannot contain any substituent. The preferred five-membered heteroaromatic rings contain 2 or 3 heteroatoms with thiazolyl, imidazolyl, oxazolyl, and thiadiazolyl being especially preferred. The preferred six-membered heteroaromatic rings include, for example, pyridinyl, pyrimidinyl, pyrazinyl, pyridazinyl, and triazinyl.

As used herein, "heterocycle" signifies a mono-, bi-, or tricyclic ring consisting of carbon atoms and from one heteroatom to the maximum number designated, wherein the heteroatom is selected from oxygen, nitrogen, and sulphur. If sulphur is present, then it can be S, S(O), or S(O)$_2$. If nitrogen is present, then it can be N, NH, substituted N, or N-oxide. The heterocycle is a non-aromatic ring, but may contain ring double bonds. If the heterocycle is monocyclic, then from 0-2 ring double bonds may be present. If the heterocycle is bicyclic, then from 0-4 ring double bonds may be present. If heterocycle ring is tricyclic, then from 0-6 ring double bonds may be present. Preferred heterocycles include, but are not limited to, pyrrolidine, piperidine, piperazine, homopiperazine, and morpholine.

As used herein, "heteroaryl" signifies a mono-, bi-, or tricyclic aromatic ring consisting of carbon atoms and from one heteroatom to the maximum number designated, wherein the heteroatom is selected from oxygen, nitrogen, and sulphur. If sulphur is present, then it can be S, S(O), or S(O)$_2$. If nitrogen is present, then it can be N, NH, substituted N, or N-oxide. If the heteroaryl is bicyclic, then one or both of the rings may have a heteroatom(s) present. If the heteroaryl is tricyclic, then one, two, or all three of the rings may have a heteroatom(s) present. If the heteroaryl is bicyclic, then one or both of the two rings may be aromatic. If the heteroaryl is tricyclic, then one, two, or all three of the two rings may be aromatic.

Examples of "heteroaryl" include, but are not limited to thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxazo-5-yl), isothiazolyl (isothiazo-3-yl, isothiazo-4-yl, isothiazo-5-yl) thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), purinyl, and tetrazolyl (5-tetrazolyl, N-tetrazolyl).

As used herein, "therapeutically effective amount" is intended to include an amount of a compound of the present invention that is effective when administered alone or in combination to activate glucokinase.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, e.g., arresting or slowing its development; and/or (c) relieving the disease-state, e.g., causing regression of the disease state itself or some symptom of the disease state.

Utility

Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM MgCl$_2$, 2 mM dithiothreitol, 0.6 mM NADP, 1 mM ATP, 0.195 µM G-6-P dehydrogenase (from Roche, 127 671), and 15 nM recombinant human glucokinase. The glucokinase is human liver glucokinase N-terminally truncated with an N-terminal His-tag ((His)$_8$-VEQILA . . . Q466) and is expressed in *E. coli* as a soluble protein with enzymatic activity comparable to liver extracted GK.

The purification of His-tagged human glucokinase (hGK) was performed as follows: The cell pellet from 50 mL *E. coli* culture was resuspended in 5 mL extraction buffer A (25 mM HEPES, pH 8.0, 1 mM MgCl$_2$, 150 mM NaCl, 2 mM mercaptoethanol) with the addition of 0.25 mg/mL lysozyme and 50 µg/mL sodium azide. After 5 minutes at room temperature, 5 mL of extraction buffer B (1.5 M NaCl, 100 mM CaCl$_2$, 100 mM MgCl$_2$, 0.02 mg/mL DNase 1, protease inhibitor tablet (Complete® 1697498): 1 tablet pr. 20 mL buffer) was added. The extract was then centrifugated at 15.000 g for 30 minutes. The resulting supernatant was loaded on a 1 mL Metal Chelate Affinity Chromatography (MCAC) Column charged with Ni$^{2+}$. The column was washed with 2 volumes buffer A containing 20 mM imidazole and the bound his-tagged hGK was subsequently eluted using a 20 minute gradient of 20 to 500 mM imididazol in buffer A. Fractions were examined using SDS-gel-electrophoresis, and fractions containing hGK (MW: 52 KDa) were pooled. Finally a gelfiltration step was used for final polishing and buffer exchange. hGK containing fractions were loaded onto a Superdex® 75 (16/60) gelfiltration column and eluted with Buffer B (25 mM HEPES, pH 8.0, 1 mM MgCl$_2$, 150 mM NaCl, 1 mM Dithiothreitol). The purified hGK was examined by SDS-gel electrophoresis and MALDI mass spectrometry and finally 20% glycerol was added before freezing. The yield from 50 mL *E. coli* culture was generally approximately 2-3 mg hGK with a purity >90%.

The compound to be tested was added into the well in final 2.5% DMSO concentration in an amount sufficient to give a desired concentration of compound, for instance 1, 5, 10, 25 or 50 µM. The reaction started after glucose was added to a final concentration of 2, 5, 10 or 15 mM. The assay used a 96-well UV plate and the final assay volume used was 200 µl/well. The plate was incubated at 25° C. for 5 min and kinetics was measured at 340 nm in SpectraMax® every 30 seconds for 5 minutes. Results for each compound were expressed as the fold activation of the glucokinase activity compared to the activation of the glucokinase enzyme in an assay without compound after having been subtracted from a "blank", which is without glucokinase enzyme and without compound. The compounds in each of the Examples exhibited activation of glucokinase in this assay. A compound, which at a concentration of at or below 30 µM gives 1.5-fold higher glucokinase activity than the result from the assay without compound, was deemed to be an activator of glucokinase.

The glucose sensitivity of the compounds was measured at a compound concentration of 10 µM and at glucose concentrations of 5 and 15 mM.

Glucokinase Activity Assay (II)

Determination of Glycogen Deposition in Isolated Rat Hepatocytes:

Hepatocytes were isolated from rats fed ad libitum by a two-step perfusion technique. Cell viability, assessed by trypan blue exclusion, was consistently greater than 80%. Cells were plated onto collagen-coated 96-well plates in basal medium (Medium 199 (5.5 mM glucose) supplemented with 0.1 µM dexamethasone, 100 units/mL penicillin, 100 mg/mL streptomycin, 2 mM L-glutamine and 1 nM insulin with 4% FCS at a cell density of 30,000 cells/well. The medium was replaced with basal medium 1 hour after initial plating in order to remove dead cells. Medium was changed after 24 hours to basal medium supplemented with 9.5 mM glucose and 10 nM insulin to induce glycogen synthesis, and experiments were performed the next day. The hepatocytes were washed twice with prewarmed (37° C.) buffer A (117.6 mM NaCl, 5.4 mM KCl, 0.82 mM Mg$_2$SO$_4$, 1.5 mM KH$_2$PO$_4$, 20 mM HEPES, 9 mM NaHCO$_3$, 0.1% w/v HSA, and 2.25 mM CaCl$_2$, pH 7.4 at 37° C.) and incubated in 100 µL buffer A containing 15 mM glucose and increasing concentrations of the test compound, such as for instance 1, 5, 10, 25, 50 or 100 µM, for 180 minutes. Glycogen content was measured using standard procedures (Agius, L. et al, Biochem J. 266, 91-102 (1990)). A compound, which when used in this assay gives a significant increase in glycogen content compared to the result from the assay without compound, was deemed to have activity in this assay.

Glucokinase Activity Assay (III)

Stimulation of Insulin Secretion by Glucokinase Activators in INS-1E Cells

The glucose responsive β-cell line INS-1E was cultivated as described by Asfari M et al., Endocrinology, 130, 167-178 (1992). The cells were then seeded into 96 well cell culture plates and grown to a density of approximately 5×10$^4$ per well. Stimulation of glucose dependent insulin secretion was tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 µM, and the supernatants were collected for measurements of insulin concentrations by ELISA (n=4). A compound, which when used in this assay gives a significant increase in insulin secretion in response to glucose compared to the result from the assay without compound, was deemed to have activity in this assay.

Synthesis

The present invention also provides a method for the synthesis of compounds useful as intermediates in the preparation of compounds of formula (I) along with methods for the preparation of compounds of formula (I). The compounds can be prepared readily according to the examples. The compounds of the present invention can also be prepared by methods known to those of skill in the art. For example, US2004/0014968, the contents of which are incorporated herein by reference, provides useful synthetic methods.

This invention will be better understood from the following examples, which are for purposes of illustration and are not intended to limit the invention defined in the claims which follow thereafter.

EXAMPLES

The following instrumentation is used:
Agilent series 1100 G1312A Bin Pump
Agilent series 1100 Column compartment
Agilent series 1100 G1315A DAD diode array detector
Agilent series 1100 MSD
Sedere 75 Evaporative Light Scattering detector
The instrument is controlled by HP Chemstation software.
The HPLC pump is connected to two eluent reservoirs containing:

| A: | 0.05% TFA in water |
| B: | 0.05% TFA in acetonitrile |

The analysis is performed at 40° C. by injecting an appropriate volume of the sample (preferably 1 µl) onto the column which is eluted with a gradient of acetonitrile.

The HPLC conditions, detector settings and mass spectrometer settings used are given in the following table.

| Column | Waters Xterra MS C-18 × 3 mm id 5 µm |
|---|---|
| Gradient | 5%-100% acetonitrile linear during 7.5 min at 1.5 mL/min |
| Detection | 210 nm (analogue output from DAD) ELS (analogue output from ELS) |
| MS | ionisation mode API-ES |

Scan 100-1000 amu step 0.1 amu
List of Abbreviations
TFA—Trifluoroacetic acid
DIPEA—Diisopropylethylamin
DIC—1,3-Diisopropyl carbodiimide
DCC—1,3-Dicyclohexyl carbodiimide
HOBt—N-Hydroxybenzotriazole
DCM—Dichloromethane
DMF—N,N-Dimethylformamide
TEA—Triethylamine
THF—Tetrahydrofuran Example 1

{2-[3-Cyclopentyl-2-(4-methanesulfonyl-phenyl)-propionylamino]-5-methyl-thiazol-4-yl}-acetic acid ethyl ester (Compound 1)

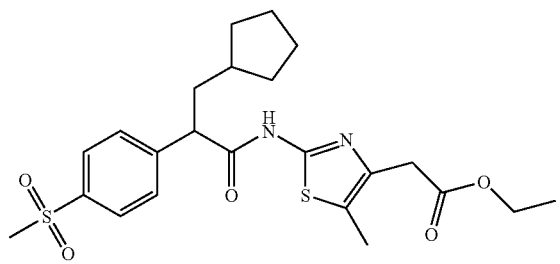

Iodomethylcyclopentane: Methanesulfonyl chloride (13.8 mL, 178 mmol) was added drop wise and at 0° C. to a solution of cyclopentanemethanol (16.2 g, 162 mmol) in anhydrous pyridine (35 mL). The mixture was stirred at 0° C. for 5 h, poured into water (200 mL), and extracted with methylene chloride (3×50 mL). The combined organic layers were washed with 1 M HCl (3×20 mL) and brine (2×20 mL), dried with anhydrous magnesium sulphate, and evaporated in vacuo. The residue was dissolved in anhydrous acetone (20 mL), and a solution of sodium iodide (24 g, 162 mmol) in acetone (50 mL) was added. The mixture was refluxed for 5 h. The formed precipitate was filtered off, and the filtrate was evaporated in vacuo. The residue was distilled and the fraction boiling at 71-75° C. (110 Torr) was collected to give iodomethylcyclopentane. Yield: 13.8 g (41%). $^1$H-NMR (CDCl$_3$, δ ppm): 3.21 (d, J=6.9 Hz, 2H); 2.18 (hept, J=7.5 Hz, 1H); 1.95-1.45 (m, 6H); 1.35-1.11 (m, 2H).

Methyl 4-(methanesulfonyl)phenyl acetate: A solution of 4-(methanesulfonyl)phenyl acetic acid (21.8 g, 101 mmol), methanol (250 mL), and concentrated sulfuric acid (1 mL) was heated under reflux for 16 h. The reaction mixture was allowed to cool to 25° C. and evaporated to dryness in vacuo. The residue was taken up in 10% aqueous sodium bicarbonate (200 mL) and ethyl acetate (200 mL). The isolated water phase was extracted with further ethyl acetate (2×200 mL), and the combined organic phases were washed with water (100 mL), dried with anhydrous sodium sulphate, and evaporated to dryness in vacuo to give methyl 4-(methanesulfonyl) phenyl acetate. Yield: 24.0 g (100%). $^1$H-NMR (CDCl$_3$, δ ppm): 7.91 (d, 2H); 7.50 (d, 2H); 3.74 (s, 2H); 3.73 (s, 3H); 3.05 (s, 3H).

Methyl 3-cyclopentyl-2-(4-methanesulfonylphenyl)propionate: Diisopropylamine (8.9 mL, 63 mmol) and 1,3-dimethyl-3,4,5,6-tetrahydro-2(1H)-pyrimidinone (18 mL) in dry tetrahydrofuran (60 mL) were cooled to -78° C. A 1.6 M solution of butyllithium in hexane (39 mL, 63 mmol) was added slowly, and the mixture was stirred at -78° C. for 0.5 h. A solution of methyl 4-(methanesulfonyl)phenyl acetate (13.69 g, 60 mmol) and 1,3-dimethyl-3,4,5,6-tetrahydro-2 (1H)-pyrimidinone (18 mL) in dry tetrahydrofuran (60 mL) was added slowly. The reaction mixture was stirred at -78° C. for 0.5 h, and a solution of iodomethylcyclopentane (13.8 g, 66 mmol) in tetrahydrofuran (10 mL) was added slowly. The mixture was then stirred at -78° C. for 0.5 h and then allowed to warm to ambient temperature where it stayed overnight. The reaction mixture was quenched with water (30 mL) and subsequently concentrated in vacuo to remove tetrahydrofuran. The residue was diluted with ethyl acetate (500 mL), washed with brine (2×100 mL), dried with anhydrous sodium sulphate, and concentrated in vacuo. Column chromatography of the residue (Silica gel, hexane/ethyl acetate (75:25)) afforded methyl 3-cyclopentyl-2-(4-methanesulfonylphenyl) propionate as an oil. Yield: 12.24 g (65%). $^1$H-NMR (CDCl$_3$, δ ppm): 7.90 (d, J=8.2 Hz, 2H); 7.53 (d, J=8.2 Hz, 2H); 3.72 (t, J=7.8 Hz, 1H); 3.67 (s, 3H); 3.07 (s, 3H); 2.21-2.05 (m, 1H); 1.95-1.70 (m, 8H); 0.95-1.25 (m, 2H).

3-Cyclopentyl-2-(4-methanesulfonylphenyl)propionic acid: A mixture of methyl 3-cyclopentyl-2-(4-methanesulfonylphenyl)propionic acid (2.8 g, 9.0 mmol), 1 N sodium hydroxide (19 mL), and methanol (25 mL) was stirred at room temperature for 24 h. The reaction mixture was concentrated in vacuo to remove the methanol and 2 N HCl (9 mL) was slowly added at 0° C. to give white crystals of 3-cyclopentyl-2-(4-methanesulfonylphenyl)propionic acid. Yield: 2.3 g (87%). mp: 160-161° C. $^1$H-NMR (CDCl$_3$, δ ppm): 7.90 (d, J=8.2 Hz, 2H); 7.54 (d, J=8.2 Hz, 2H); 3.72 (t, J=7.8 Hz, 1H); 3.05 (s, 3H); 2.15-2.08 (m, 1H); 1.9-1.45 (m, 8H); 1.05-1.20 (m, 2H).

To a solution of 3-cyclopentyl-2-(4-methanesulfonylphenyl)propionic acid (200 mg, 0.67 mmol) in a mixture of dry methylene chloride (5 mL) and dry DMF (1 mL) were added HOBT (20 mg) and DCC (155 mg, 0.75 mmol), and the mixture was stirred at room temperature for 2 h. A solution of (2-amino-5-methyl-thiazol-4-yl)-acetic acid ethyl ester (220 mg, 0.78 mmol) and DIPEA (135 µl, 102 mg, 0.79 mmol) in dry DMF (1 mL) was added to the reaction mixture and stirring was continued for 18 h at room temperature. The mixture was evaporated in vacuo and the residue purified on a silica gel column (heptan:ethyl acetate (7:3)) to give {2-[3-cyclopentyl-2-(4-methanesulfonyl-phenyl)-propionylamino]-5-methyl-thiazol-4-yl}-acetic acid ethyl ester. Yield: 120 mg (37%). $^1$H-NMR (CDCl$_3$): δ 8.86 (broad s, 1H), 7.91 (d, 2H), 7.52 (d, 2H), 4.14 (q, 2H), 3.66 (t, 1H), 3.57 (s, 2H), 3.07 (s, 3H), 2.32 (s, 3H), 2.25-2.18 (m, 1H), 1.93-1.86 (m, 1H), 1.81-1.43 (m, 7H), 1.24 (t, 3H), 1.16-1.06 (m, 2H); HPLC-MS: m/z=480 (M+1); $R_t$=4.09 min.

Example 2

3-Cyclopentyl-2-(4-methanesulfonyl-phenyl)-N-[4-methyl-5-(4-methyl-piperazine-1-sulfonyl)-thiazol-2-yl]-propionamide (Compound 2)

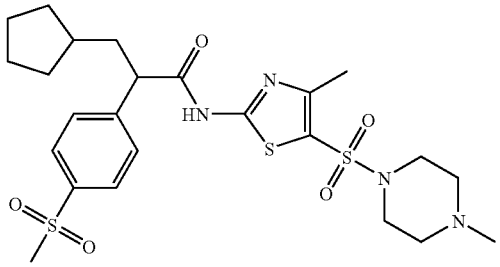

N-[5-(4-Methylpiperazine-1-sulfonyl)-thiazol-2-yl]-acetamide: To a solution of 2-acetamido-4-methyl-5-thiazolesulfonyl chloride (3 g, 11.8 mmol) in DCM (50 mL) and TEA (3.2 mL, 23.6 mmol) was slowly added N-methylpiperazine (1.2 g, 12.4 mmol). The reaction mixture was stirred at room temperature for 2 hours. Water (50 mL) was added, and the organic phase was isolated. The water phase was extracted with DCM (3×75 mL). The combined organic phase was dried with anhydrous magnesium sulphate, filtered, and evaporated in vacuo to give 2.6 g of yellow, impure crystals. Purification on a silica gel column (Eluent: DCM:MeOH (9:1)) gave N-[5-(4-methylpiperazine-1-sulfonyl)-thiazol-2-yl]-acetamide as light yellow crystals of N-[5-(4-methylpiperazine-1-sulfonyl)-thiazol-2-yl]-acetamide. Yield: 1.52 g (41%). $^1$H-NMR (CDCl$_3$): δ3.20 (m, 4H); 2.55 (m, 7H); 2.32 (s, 3H); 2.29 (s, 3H).

4-Methyl-5-(4-methyl-piperazine-1-sulfonyl)-thiazol-2-ylamine: A solution of N-[5-(4-methylpiperazine-1-sulfonyl)-thiazol-2-yl]-acetamide (1 g, 3.1 mmol) in methanol (5 mL) and 6 N hydrochloric acid (5 mL) was heated in a microwave oven (4×5 min at 80° C.). The reaction mixture was partly evaporated to remove most of the methanol, and the residue was washed with DCM (10 mL). The water phase was isolated, and the pH adjusted to 8-9. Extraction with DCM (3×25 mL), drying over anhydrous magnesium sulphate, and evaporation in vacuo gave white crystals of 4-methyl-5-(4-methyl-piperazine-1-sulfonyl)-thiazol-2-ylamine. Yield: 0.53 g (61%). $^1$H-NMR (CDCl$_3$): δ 5.46 (m, 2H); 3.18 (m, 4H); 2.51 (m, 4H); 2.45 (s, 3H); 2.31 (s, 3H).

3-Cyclopentyl-2-(4-methanesulfonyl-phenyl)-N-[4-methyl-5-(4-methylpiperazine-1-sulfonyl)-thiazol-2-yl]-propionamide was prepared from 3-cyclopentyl-2-(4-methanesulfonylphenyl)propionic acid and 4-methyl-5-(4-methylpiperazine-1-sulfonyl)-thiazol-2-ylamine as described in Example 1. $^1$H-NMR (CDCl$_3$): δ 13.03 (broad s, 1H), 7.91 (d, 2H), 7.64 (d, 2H), 4.05 (t, 1H), 3.20 (s, 3H), 2.99 (m, 4H), 2.47 (s, 3H), 2.39 (m, 4H), 2.16 (m, 4H), 1.84-1.77 (m, 1H), 1.75-1.39 (m, 7H), 1.19-1.07 (m, 2H); HPLC-MS: m/z=555 (M+1); $R_t$=3.08 min.

Example 3

3-Cyclopentyl-2-(4-methanesulfonyl-phenyl)-N-[5-(4-methyl-piperazin-1-yl)-thiazol-2-yl]-propionamide (Compound 3)

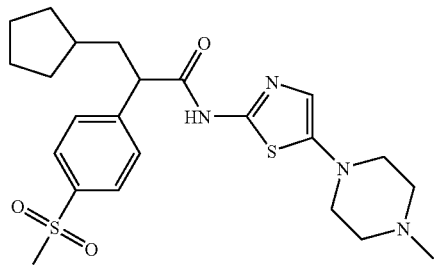

2-Amino-5-(4-methyl-piperazin-1-yl)-thiazole: To a solution of 2-amino-5-bromothiazol, HBr (500 mg, 1.9 mmol) in DMF (6 mL) were added potassium carbonate, anhydrous (1.0 g, 7.3 mmol) and N-methylpiperazine (215 µL, 1.9 mmol). The reaction mixture was stirred at room temperature for 2 hours and then filtered and evaporated to dryness in vacuo. Stirring of the residue with ethyl acetate (3 mL) gave beige crystals of 2-amino-5-(4-methyl-piperazin-1-yl)-thiazole. Yield: 290 mg (76%). $^1$H-NMR (CD$_3$OD): δ 6.34 (s, 1H), 2.94 (t, 4H), 2.56 (t, 4H), 2.32 (s, 3H).

3-Cyclopentyl-2-(4-methanesulfonyl-phenyl)-N-[5-(4-methyl-piperazin-1-yl)-thiazol-2-yl]-propionamide was prepared from 3-cyclopentyl-2-(4-methanesulfonylphenyl)propionic acid and 2-amino-5-(4-methyl-piperazin-1-yl)thiazole as described in Example 1. $^1$H-NMR (CD$_3$OD): δ 7.92 (d, 2H), 7.68 (d, 2H), 6.80 (s, 1H), 3.95 (t, 1H), 3.57 (m, 4H), 3.29 (m, 2H), 3.16 (m, 2H), 3.11 (s, 3H), 2.95 (s, 3H), 2.22-2.15 (m, 1H), 1.88-1.43 (m, 8H), 1.21-1.11 (m, 2H); HPLC-MS: m/z=477 (M+1).

Example 4

{2-[3-Cyclopentyl-2-(4-methanesulfonyl-phenyl)-propionylamino]-thiazol-5-ylsulfanyl}-acetic acid ethyl ester (Compound 4)

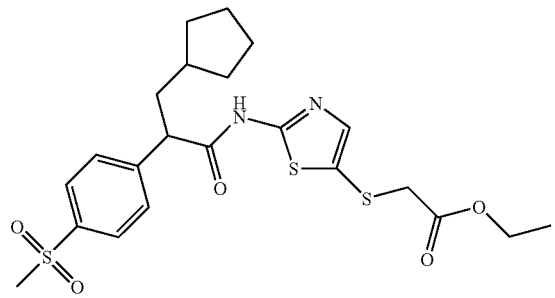

(2-Aminothiazol-5-ylsulfanyl)-acetic acid ethyl ester: A mixture of 2-amino-5-bromothiazole, HBr (7.26 g, 27.9 mmol), ethyl thioglycolate (10 g, 83.8 mmol), and potassium carbonate (7.7 g, 55.9 mmol) in DMF (25 mL) was stirred at room temperature for 2 hours. The reaction mixture was filtered and water (150 mL) and ethyl acetate (400 mL) were added. The organic phase was isolated and washed with brine (3×50 mL), dried over anhydrous magnesium sulphate, and evaporated to dryness in vacuo to give (2-aminothiazol-5-ylsulfanyl)-acetic acid ethyl ester. Yield: 3.3 g (54%). $^1$H-NMR (DMSO-$d_6$): δ 7.6 (s, 2H), 7.00 (s, 1H), 4.08 (q, 2H), 3.45 (s, 2H), 1.17 (t, 3H).

{2-[3-Cyclopentyl-2-(4-methanesulfonyl-phenyl)-propionylamino]-thiazol-5-ylsulfanyl}-acetic acid ethyl ester was prepared from 3-cyclopentyl-2-(4-methanesulfonylphenyl) propionic acid and (2-aminothiazol-5-ylsulfanyl)-acetic acid ethyl ester as described in Example 1. $^1$H-NMR (CDCl$_3$): δ 11.78 (broad s, 1H), 7.88 (d, 2H), 7.57 (d, 2H), 7.54 (s, 1H), 4.18 (q, 2H), 3.80 (t, 1H), 3.46 (s, 2H), 3.05 (s, 3H), 2.31-2.23 (m, 1H), 1.92-1.85 (m, 1H), 1.80-1.40 (m, 7H), 1.26 (t, 3H), 1.12 (m, 2H); HPLC-MS: m/z=497 (M+1).

Example 5

{5-Chloro-2-[3-cyclopentyl-2-(4-methanesulfonyl-phenyl)propionylamino]-thiazol-4-yl}-acetic acid ethyl ester (Compound 5)

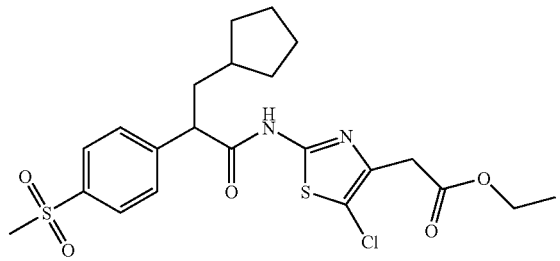

(2-Amino-5-chloro-thiazol-4-yl)-acetic acid ethyl ester: To a solution of (2-aminothiazol-4-yl)-acetic acid ethyl ester (2.2 g, 11.8 mmol) in acetic acid (200 mL) was added N-chlorosuccinimide (1.73 g, 13.0 mmol), and the mixture was stirred at room temperature for 3 hours. The solvent was removed in vacuo, and the residue was stirred with acetone to give crystals of 2-amino-5-chloro-thiazol-4-yl)-acetic acid ethyl ester, HCl. Yield: 1.45 g (48%). $^1$H-NMR (DMSO-$d_6$): δ 4.08 (q, 2H), 3.60 (s, 2H), 1.17 (t, 3H).

{5-Chloro-2-[3-cyclopentyl-2-(4-methanesulfonyl-phenyl)propionylamino]-thiazol-4-yl}-acetic acid ethyl ester was prepared from 3-cyclopentyl-2-(4-methanesulfonylphenyl)propionic acid and 2-amino-5-chloro-thiazol-4-yl)-acetic acid ethyl ester as described in Example 1. $^1$H-NMR (CDCl$_3$): δ 9.28 (broad s, 1H), 7.91 (d, 2H), 7.53 (d, 2H), 4.15 (q, 2H), 3.72 (t, 1H), 3.65 (s, 2H), 3.08 (s, 3H), 2.24-2.17 (m, 1H), 2.01-1.46 (m, 8H), 1.25 (t, 3H), 1.16-1.06 (m, 2H); HPLC-MS: m/z=499 (M+1).

Example 6

{2-[3-Cyclopentyl-2-(4-methanesulfonyl-phenyl)-propionylamino]-5-methyl-thiazol-4-yl}-acetic acid (Compound 6)

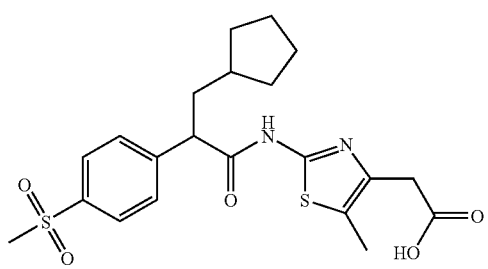

{2-[3-Cyclopentyl-2-(4-methanesulfonylphenyl)-propionylamino]-5-methyl-thiazol-4-yl}-acetic acid ethyl ester (49 mg, 0.1 mmol), dioxan (0.5 mL), and 1 N sodium hydroxide were stirred at room temperature for 20 h. The pH was adjusted to approx. 3 with 1 N hydrochloric acid (0.5 mL), the reaction mixture was concentrated in vacuo, and the precipitate was isolated by filtration. Yellow crystals of the title compound were washed with water and dried to give 43 mg (yield: 93%). $^1$H-NMR (CDCl$_3$): δ 7.85 (d, 2H), 7.58 (d, 2H), 3.78 (t, 1H), 3.62 (s, 2H), 3.01 (s, 3H), 2.42 (s, 3H), 2.22-2.15 (m, 1H), 1.93-1.86 (m, 1H), 1.75-1.49 (m, 7H), 1.15-1.02 (m, 2H); HPLC-MS: m/z=451 (M+1).

Example 7

{2-[3-Cyclopentyl-2-(4-methanesulfonyl-phenyl)-propionylamino]-thiazol-5-ylsulfanyl}-acetic acid (Compound 7)

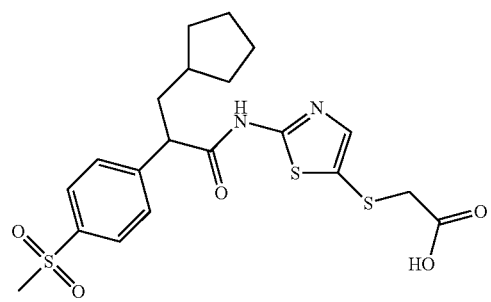

The title compound was prepared as described in Example 6. $^1$H-NMR (CDCl$_3$): δ 7.90 (d, 2H), 7.62 (d, 2H), 7.38 (s, 1H), 3.82 (t, 1H), 3.47 (s, 2H), 3.05 (s, 3H), 2.26-2.19 (m, 1H), 1.96-1.89 (m, 1H), 1.80-1.42 (m, 7H), 1.20-1.07 (m, 2H); HPLC-MS: m/z=469 (M+1).

Example 8

{5-Chloro-2-[3-cyclopentyl-2-(4-methanesulfonyl-phenyl)propionylamino]-thiazol-4-yl}-acetic acid (Compound 8)

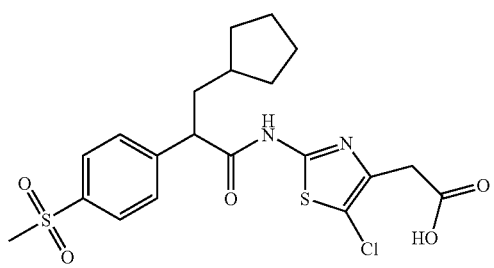

The title compound was prepared as described in example 6. $^1$H-NMR CDCl$_3$): δ 7.87 (d, 2H), 7.58 (d, 2H), 3.77 (t, 1H), 3.69 (s, 2H), 3.03 (s, 3H), 2.21-2.14 (m, 1H), 1.95-1.88 (m, 1H), 1.77-1.41 (m, 7H), 1.16-1.03 (m, 2H); HPLC-MS: m/z=471/473 (3:1; M+1).

Example 9

(R)-3-Cyclopentyl-2-(4-methanesulfonyl-phenyl)-N-(5-thiocyanato-thiazol-2-yl)-propionamide (Compound 9)

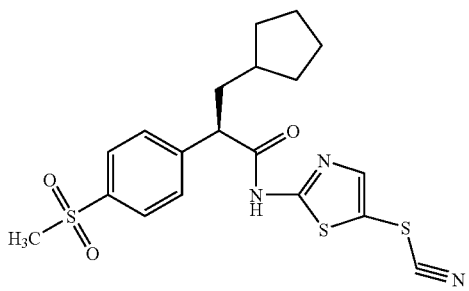

(4S,2'R)-4-benzyl-3-[3-cyclopentyl-2-(4-methanesulfonyl phenyl) propionyl]oxazolidin-2-one: A solution of (S)-(−)-4-benzyl-2-oxazolidinone (8.70 g, 49 mmol) in dry THF (70 mL) was cooled to −78° C. and then treated with a 1.6 M solution of butyllithium in hexanes (29 mL, 47 mmol). The solution was stirred at −78° C. for 0.5 h and then allowed to warm to 25° C. where it was stirred for 1 h. Parallel to it; a solution of racemic 3-cyclopentyl-2-(4-methanesulfonylphenyl)propionic acid (11.63 g, 39 mmol) in dry THF (83 mL) was cooled to 0° C. and TEA (6.7 mL, 47 mmol) was added. Trimethylacetyl chloride (5.9 g, 49 mmol) was added drop wise and the reaction mixture was stirred at 0° C. for 2 h and then cooled to −78° C. The mixture containing the oxazolidinone was then added to the cold mixed anhydride solution. The resulting mixture was stirred at −78° C. for 1 h and then stirred at ambient temperature overnight. The resulting mixture was quenched with water (250 mL) and then concentrated in vacuo to remove TFH. The aqueous residue was extracted with ethyl acetate (3×250 mL). The combined organic layers were washed with brine (3×100 mL), dried with anhydrous sodium sulphate and evaporated in vacuo. The diastereoisomers were separated by flash column chromatography (silica gel, hexane/ethyl acetate 75:25) affording the higher moving product, (4S,2'R)-4-benzyl-3-[3-cyclopentyl-2-(4-methanesulfonyl phenyl) propionyl]oxazolidin-2-one. Yield 6.2 g (34%). $^1$H NMR (CDCl$_3$): δ 7.92 (d, J=8.3 Hz, 2H); 7.66 (d, J=8.3 Hz, 2H); 7.24-7.18 (m, 3H); 7.02-6.93 (m, 2H); 5.17 (t, J=7.5 Hz, 1H); 4.80-4.65 (m, 1H); 4.30-4.05 (m, 2H); 3.22-3.05 (m, 1H); 3.08 (s, 3H); 2.58 (dd, J=9.4 and 13.6 Hz, 1H); 2.22-2.02 (m, 1H); 1.95-1.35 (m, 8H); 1.30-1.00 (m, 2H).

(2R)-3-cyclopentyl-2-(4-methanesulfonylphenyl)propionic acid: An aqueous solution of lithium hydroperoxide was prepared by mixing a solution of lithium hydroxide monohydrate (1.4 g, 33 mmol) in water (7 mL) and 30% aqueous hydrogen peroxide (6.8 mL, 66 mmol). The solution was cooled to 0° C. and then slowly added to a solution of (4S,2'R)-4-benzyl-3-[3-cyclopentyl-2-(4-methanesulfonyl phenyl) propionyl]oxazolidin-2-one (7.15 g, 15.7 mmol) in THF (45 mL) and water (15 mL). The reaction mixture was stirred at 0° C. for 1.5 h, quenched with saturated aqueous sodium sulphite solution (20 mL) and diluted with water (300 mL). The aqueous layer was washed with diethyl ether (4×200 mL), acidified with HCl to pH=2, and extracted with ethyl acetate (3×200 mL). The ethyl acetate phases were dried with anhydrous sodium sulphate and evaporated to dryness in vacuo to give (2R)-3-cyclopentyl-2-(4-methanesulfonylphenyl)propionic acid. Yield: 4.59 g (98%). mp: 132-141° C. $^1$H-NMR (CDCl$_3$): δ 7.90 (d, 2H); 7.54 (d, 2H); 3.72 (t, 1H); 3.06 (s, 3H); 2.20-2.03 (m, 1H); 1.95-1.40 (m, 8H); 1.30-1.00 (m, 2H). [α]$^{23}$=−50.0° (c=0.02 g/100 mL, chloroform).

The title compound was prepared from (2R)-3-cyclopentyl-2-(4-methanesulfonylphenyl)propionic acid and 2-amino-5-thiocyanothiazole as described in Example 1. $^1$H-NMR (CDCl$_3$): δ 7.92 (d, 2H), 7.71 (s, 1H), 7.55 (d, 2H), 3.77 (t, 1H), 3.07 (s, 3H), 2.29-2.21 (m, 1H), 1.98-1.89 (m, 1H), 1.82-1.69 (m, 2H), 1.67-1.57 (m, 3H), 1.53-1.47 (m, 2H), 1.19-1.08 (m, 2H); HPLC-MS: m/z=436 (M+1).

Example 10

(R)-3-Cyclopentyl-N-[5-(2-diethylamino-ethylsulfanyl)-thiazol-2-yl]-2-(4-methanesulfonyl-phenyl)-propionamide (Compound 10)

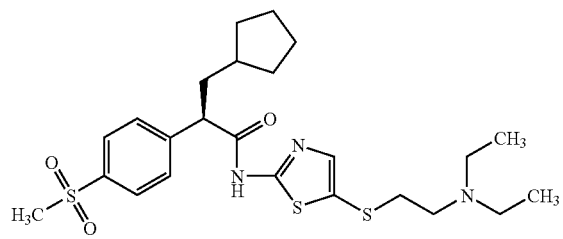

To a solution of (R)-3-cyclopentyl-2-(4-methanesulfonylphenyl)-N-(5-thiocyanato-thiazol-2-yl)-propionamide (200 mg, 0.46 mmol) in methanol (2.5 mL) and DCM (2.5 mL) was added dithiothreitol (71 mg, 0.46 mmol), and the mixture was stirred at room temperature for 1 h. 2-Chloroethyl-diethylamine (158 mg, 0.92 mmol), potassium carbonate (235 mg, 0.46 mmol), and potassium iodide (10 mg) were added and the reaction mixture was stirred for another 3 h at room temperature. Water (5 mL) and DCM (10 mL) were added and the organic phase was isolated and dried over anhydrous magnesium sulphate. The solvent was removed in vacuo, and the residue was purified on a silica gel column (isocratic from 100% DMC to 100% ethyl acetate with 1% TEA) to give colourless crystals of (R)-3-cyclopentyl-N-[5-(2-diethylamino-ethylsulfanyl)-thiazol-2-yl]-2-(4-methanesulfonylphenyl)-propionamide. Yield: 150 mg (64%). $^1$H-NMR (CDCl$_3$): δ 11.50 (broad s, 1H), 7.86 (d, 2H), 7.51 (d, 2H), 7.48 (s, 1H), 3.76 (t, 1H), 3.04 (s, 3H), 2.86 (t, 2H), 2.71 (t, 2H), 2.54 (q, 4H), 2.26 (m, 1H), 1.90 (m, 1H), 1.79-1.43 (m, 8H), 1.12 (m, 1H), 1.00 (t, 6H); HPLC-MS: m/z=510 (M+1).

Example 11

(R)-3-Cyclopentyl-2-(4-methanesulfonyl-phenyl)-N-(5-methylsulfanyl-thiazol-2-yl)-propionamide (Compound 11)

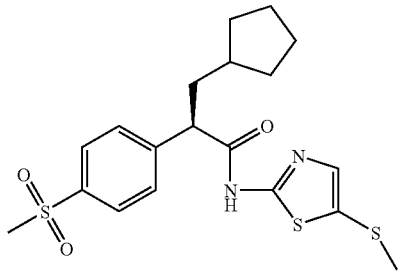

The title compound was prepared from (R)-3-cyclopentyl-2-(4-methanesulfonyl-phenyl)-N-(5-thiocyanato-thiazol-2-yl)-propionamide and methyl iodide as described in Example 10. ¹H-NMR (CDCl₃): δ 11.8 (broad s, 1H), 7.86 (d, 2H), 7.52 (d, 2H), 7.44 (s, 1H), 3.79 (t, 1H), 3.04 (s, 3H), 2.46 (s, 3H), 2.27 (m, 1H), 1.89 (m, 1H), 1.81-1.44 (m, 7H), 1.12 (m, 2H); HPLC-MS: m/z: 425 (M+1).

Example 12

3-Cyclopentyl-N-(5-diethylcarbamoylmethylsulfanyl-thiazol-2-yl)-2-(4-methanesulfonyl-phenyl)-propionamide (Compound 12)

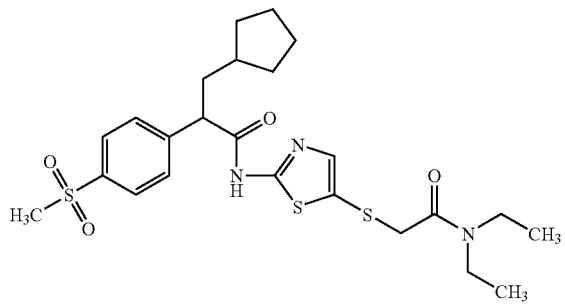

To a solution of {2-[3-cyclopentyl-2-(4-methanesulfonyl-phenyl)propionylamino]-thiazol-5-ylsulfanyl}-acetic acid (33 mg, 70.4 mmol) in DMF (0.5 mL) was added 3-hydroxy-1,2,3-benzotriazin-4-(3H)-one (12 mg, 73.5 mmol) and 1-(3-dimethylaminopropyl)-3-ethylcarbodiimide hydrochloride (14 mg, 73 mmol). The reaction mixture was stirred at room temperature for 2 hours after which diethyl amine (10 μL, 96.3 mmol) and DIPEA (12 μL, 70.3 mmol) were added. Stirring was continued for 20 hours. The reaction mixture was purified by HPLC (C18, gradient 25%-100% acetonitrile) to give 3-cyclopentyl-N-(5-diethylcarbamoylmethylsulfanyl-thiazol-2-yl)-2-(4-methanesulfonyl-phenyl)propionamide as an oil. Yield: 15 mg (42%). ¹H-NMR (CDCl₃): δ 7.91 (d, 2H), 7.62 (d, 2H), 7.45 (s, 1H), 3.93 (t, 1H), 3.63 (s, 3H), 3.38 (q, 2H), 3.31 (q, 2H), 3.05 (s, 3H), 2.28-2.21 (m, 1H), 1.97-1.90 (m, 1H), 1.75-1.47 (m, 7H), 1.23-1.11 (m, 8H); HPLC-MS: m/z: 525 (M+1).

Example 13

{2-[3-Cyclopentyl-2-(4-methanesulfonyl-phenyl)-propionylamino]-thiazole-5-sulfonyl}-acetic acid (Compound 13)

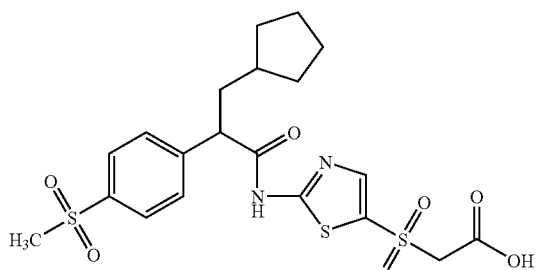

To a mixture of montmorillonite KSF (150 mg), water (50 μL), DCM (0.5 mL), and oxone (105 mg) was added a solution of {2-[3-cyclopentyl-2-(4-methanesulfonylphenyl)-propionylamino]-thiazol-5-ylsulfanyl}-acetic acid (32 mg, 68.3 mmol) in DCM (0.7 mL). The reaction mixture was stirred at room temperature for 18 hours, filtered and evaporated to dryness in vacuo to give the title compound as white crystals. Yield: 9 mg (25%). ¹H-NMR (CDCl₃): δ 7.83 (m, 3H), 7.51 (d, 2H), 4.21 (s, 2H), 3.81 (t, 1H), 3.00 (s, 3H), 2.14 (m, 1H), 1.88 (m, 1H), 1.69-1.38 (m, 8H), 1.06 (m, 2H); HPLC-MS: m/z: 501 (M+1).

Example 14

(R)-{2-[3-Cyclopentyl-2-(4-methanesulfonyl-phenyl)propionylamino]-thiazol-5-ylsulfanyl}-acetic acid ethyl ester (Compound 14)

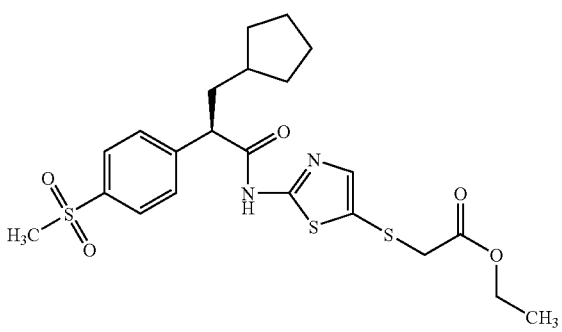

The title compound was prepared from (R)-3-cyclopentyl-2-(4-methanesulfonylphenyl)propionic acid and (2-aminothiazol-4-yl)-acetic acid ethyl ester as described in Example 1. ¹H-NMR (CDCl₃): δ 11.07 (broad s, 1H), 7.89 (d, 1H), 7.54 (m, 3H), 4.18 (q, 2H), 3.76 (t, 1H), 3.45 (s, 2H), 3.05 (s, 3H), 2.27 (m, 1H), 1.90 (m, 1H), 1.81-1.44 (m, 8H), 1.26 (t, 3H), 1.12 (m, 2H); HPLC-MS: m/z: 498 (M+1).

Example 15

(R)-{2-[3-Cyclopentyl-2-(4-methanesulfonyl-phenyl)propionylamino]-thiazol-5-ylsulfanyl}-acetic acid (Compound 15)

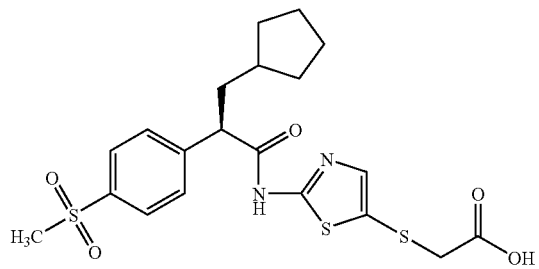

The title compound was prepared from (R)-{2-[3-Cyclopentyl-2-(4-methanesulfonyl-phenyl)-propionylamino]-thiazol-5-ylsulfanyl}-acetic acid ethyl ester as described in Example 6. ¹H-NMR (CDCl₃): δ 7.90 (d, 2H), 7.62 (d, 2H), 7.34 (s, 1H), 3.83 (t, 1H), 3.44 (s, 2H), 3.04 (s, 3H), 2.29-2.17 (m, 1H), 1.98-1.90 (m, 1H), 1.80-1.46 (m, 7H), 1.20-1.08 (m, 2H); HPLC-MS: m/z: 469 (M+1).

Example 16

(R)-3-{2-[3-Cyclopentyl-2-(4-methanesulfonyl-phenyl)propionylamino]-thiazol-5-ylsulfanyl}-propionic acid ethyl ester (Compound 16)

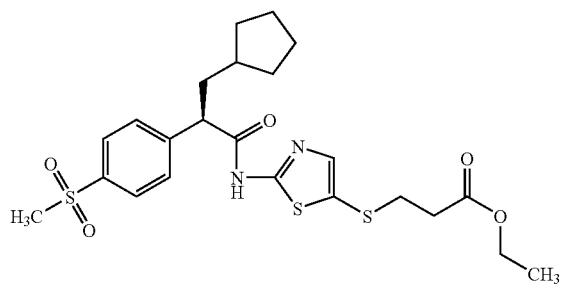

3-(2-Amino-thiazol-5-ylsulfanyl)-propionic acid ethyl ester: To a solution of 2-amino-5-bromothiazole (50 g, 192 mmol) in DMF (300 mL) were added potassium carbonate (53 g, 384 mmol) and ethyl 3-mercaptopropionate (25.8 g, 192 mmol). The reaction mixture was stirred at room temperature for 36 h. The mixture was partitioned between water (500 mL) and ethyl acetate (500 mL) and the isolated water phase was extracted with ethyl acetate (250 mL). The combinde organic phases were washed with water (250 mL) and 10% aqueous sodium hydrogencarbonate (250 mL), dried over anhydrous magnesium sulphate and evaporated to dryness in vacuo to give 3-(2-amino-thiazol-5-ylsulfanyl)-propionic acid ethyl ester. Yield: 19.6 g (44%). $^1$H-NMR (CDCl$_3$): δ 7.07 (s, 1H); 4.15 (q, 2H); 2.88 (t, 2H); 2.61 (t, 2H); 1.26 (t, 3H); HPLC-MS: m/z: 233 (M+1).

(R)-3-{2-[3-Cyclopentyl-2-(4-methanesulfonyl-phenyl)propionylamino]-thiazol-5-ylsulfanyl}-propionic acid ethyl ester was prepared from (R)-3-cyclopentyl-2-(4-methanesulfonylphenyl)propionic acid and 3-(2-aminothiazol-5-ylsulfanyl)-propionic acid ethyl ester as described in Example 1. $^1$H_NMR (CD$_3$OD): δ 7.92 (d, 2H), 7.67 (d, 2H), 7.40 (s, 1H), 4.08 (q, 2H), 3.96 (t, 1H), 3.09 (s, 3H), 2.92 (t, 2H), 2.57 (t, 2H), 2.21 (m, 1H), 1.88-1.48 (m, 8H), 1.22-1.17 (m, 5H); HPLC-MS: m/z: 511 (M+1).

Example 17

(R)-3-Cyclopentyl-2-(4-methanesulfonyl-phenyl)-N-[5-(2-oxo-2-piperazin-1-yl-ethylsulfanyl)-thiazol-2-yl]-propionamide (Compound 17)

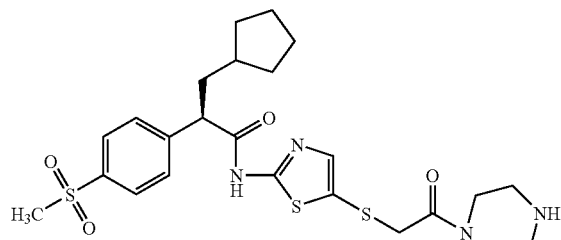

(R)-4-(2-{2-[3-Cyclopentyl-2-(4-methanesulfonyl-phenyl)propionylamino]-thiazol-5-ylsulfanyl}-acetyl)-piperazine-1-carboxylic acid tert-butyl ester was prepared from (R)-{2-[3-cyclopentyl-2-(4-methanesulfonyl-phenyl)propionylamino]-thiazol-5-ylsulfanyl}-acetic acid and tert-butyl-1-piperazinecarboxylate as described in Example 12. $^1$H-NMR (CDCl$_3$): δ 7.87 (d, 2H), 7.54 (d, 2H), 7.44 (s, 1H), 3.87 (t, 1H), 3.66 (s, 2H), 3.61-3.46 (m, 8H), 3.05 (s, 3H), 2.24 (m, 1H), 1.89 (m, 1H), 1.79-1.54 (m, 5H), 1.48 (m, 11H), 1.14 (m, 2H); HPLC-MS: m/z: 637 (M+1), 582 (M+1-C(CH$_3$)$_3$)

(R)-4-(2-{2-[3-Cyclopentyl-2-(4-methanesulfonyl-phenyl)propionylamino]-thiazol-5-ylsulfanyl}-acetyl)-piperazine-1-carboxylic acid tert-butyl ester (50 mg, 78.6 mml) was dissolved in a mixture of chloroform (2 mL) and TFA (1 mL). The mixture was stirred at room temperature for 2 h and evaporated to dryness in vacuo to give white crystals of (R)-3-cyclopentyl-2-(4-methanesulfonylphenyl)-N-[5-(2-oxo-2-piperazin-1-yl-ethylsulfanyl)-thiazol-2-yl]-propionamide.
$^1$H-NMR (CD$_3$OD): δ 7.92 (d, 2H), 7.67 (d, 2H), 7.48 (s, 1H), 3.97 (t, 1H), 3.81 (m, 4H), 3.73 (s, 3H), 3.29-3.23 (m, 4H), 3.10 (s, 3H), 2.24-2.16 (m, 1H), 1.90-1.75 (m, 3H), 1.69-1.59 (m, 3H), 1.50 (m, 2H), 1.17 (m, 2H); HPLC-MS: m/z: 537 (M+1).

Example 18

(R)-3-Cyclopentyl-2-(4-methanesulfonyl-phenyl)-N-[5-(2-morpholin-4-yl-2-oxo-ethylsulfanyl)-thiazol-2-yl]-propionamide (Compound 18)

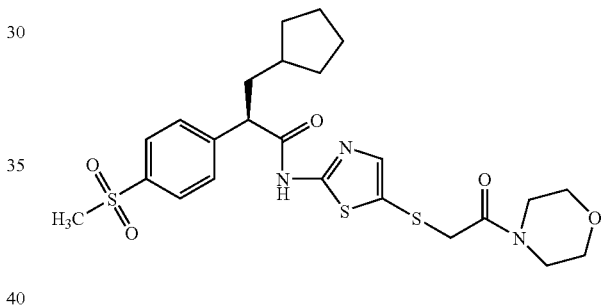

The title compound was prepared from (R)-{2-[3-cyclopentyl-2-(4-methanesulfonyl-phenyl)-propionylamino]-thiazol-5-ylsulfanyl}-acetic acid and morpholine as described in Example 12. $^1$H-NMR (CD$_3$OD): δ 7.92 (d, 2H), 7.67 (d, 2H), 7.48 (s, 1H), 3.96 (t, 1H), 3.64 (s, 2H), 3.63-3.46 (m, 8H), 3.09 (s, 3H), 2.25-2.18 (m, 1H), 1.88-1.75 (m, 3H), 1.64 (m, 3H), 1.50 (m, 2H), 1.17 (m, 2H); HPLC-MS: m/z: 538 (M+1).

Example 19

(R)-3-Cyclopentyl-2-(4-methanesulfonyl-phenyl)-N-{5-[2-(4-methyl-piperazin-1-yl)-2-oxo-ethylsulfanyl]-thiazol-2-yl}-propionamide (Compound 19)

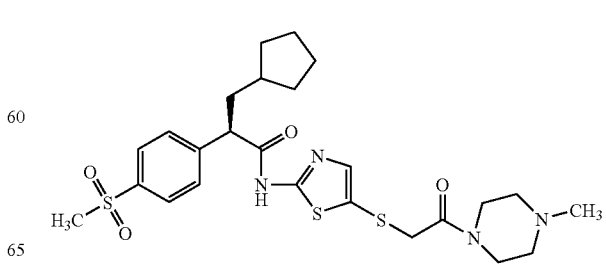

The title compound was prepared from (R)-{2-[3-cyclopentyl-2-(4-methanesulfonyl-phenyl)-propionylamino]-thiazol-5-ylsulfanyl}-acetic acid and 1-methylpiperazine as described in Example 12. ¹H-NMR (CD₃OD): δ 7.92 (d, 2H), 7.67 (d, 2H), 7.50 (s, 1H), 4.83-4.15 (broad m, 2H), 3.96 (t, 1H), 3.72 (s, 2H), 3.60-3.45 (broad m, 3H), 3.12-3.00 (broad m, 3H), 3.10 (s, 3H), 2.92 (s, 3H), 2.25-2.17 m, 1H), 1.90-1.75 (m, 3H), 1.70-1.60 (m, 3H), 1.51 (m, 2H), 1.18 (m, 2H); HPLC-MS: m/z: 551 (M+1).

Example 20

(R)-3-Cyclopentyl-2-(4-methanesulfonyl-phenyl)-N-[5-(2-oxo-2-piperidin-1-yl-ethylsulfanyl)-thiazol-2-yl]-propionamide (Compound 20)

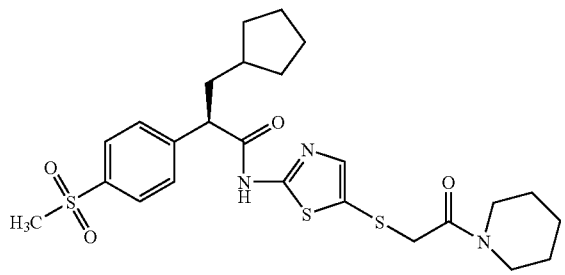

The title compound was prepared from (R)-{2-[3-Cyclopentyl-2-(4-methanesulfonyl-phenyl)-propionylamino]-thiazol-5-ylsulfanyl}-acetic acid and piperidine as described in Example 12. ¹H-NMR (CD₃OD): δ 7.92 (d, 2H), 7.66 (d, 2H), 7.46 (s, 1H), 3.96 (t, 1H), 3.63 (s, 2H), 3.48 (broad t, 2H), 3.43 (broad t, 2H), 3.09 (s, 3H), 2.25-2.18 (m, 1H), 1.88-1.48 (m, 14H), 1.17 (m, 2H); HPLC-MS: m/z: 536 (M+1).

Example 21

(R)-3-Cyclopentyl-N-[5-(2-dimethylamino-ethylsulfanyl)-thiazol-2-yl]-2-(4-methanesulfonyl-phenyl)-propionamide (Compound 21)

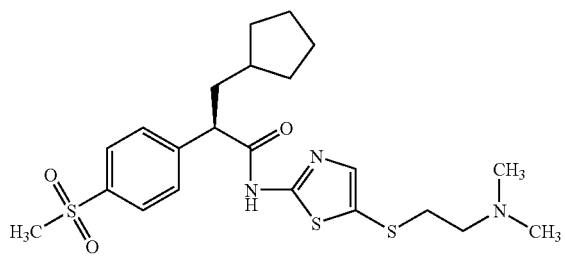

The title compound was prepared from (R)-3-cyclopentyl-2-(4-methanesulfonyl-phenyl)-N-(5-thiocyanato-thiazol-2-yl)-propionamide and 2-(dimethylamino)ethyl chloride as described in Example 10. ¹H-NMR (CD₃OD): δ 7.92 (d, 2H), 7.67 (d, 2H), 7.55 (s, 1H), 3.96 (t, 1H), 3.29 (m, 2H), 3.10 (s, 3H), 3.06 (m, 2H), 2.87 (s, 6H), 2.26-2.19 (m, 1H), 1.89-1.48 (m, 8H), 1.18 (m, 2H); HPLC-MS: m/z: 482 (M+1).

Example 22

(R)-3-Cyclopentyl-2-(4-methanesulfonyl-phenyl)-N-[5-(2-morpholin-4-yl-ethylsulfanyl)-thiazol-2-yl]-propionamide (Compound 22)

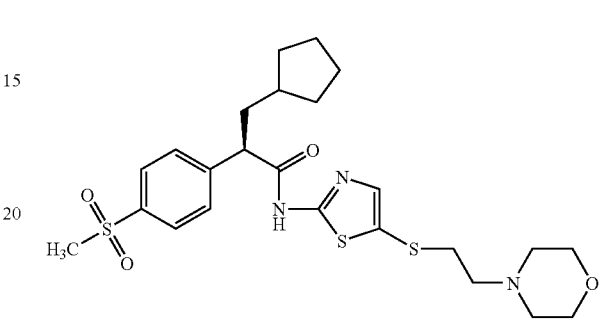

The title compound was prepared from (R)-3-cyclopentyl-2-(4-methanesulfonyl-phenyl)-N-(5-thiocyanato-thiazol-2-yl)-propionamide and 4-(2-chloroethyl)morpholine as described in Example 10. ¹H-NMR (CD₃OD): δ 7.92 (d, 2H), 7.67 (d, 2H), 7.55 (1H), 3.96 (t, 1H), 4.00-3.37 (broad m, 8H), 3.34 (m, 2H), 3.10 (s, 3H), 3.09-3.05 (m, 2H), 2.26-2.29 (m, 1H), 1.89-1.47 (m, 8H), 1.18 (m, 2H); HPLC-MS: m/z: 524 (M+1).

Example 23

(R)-3-Cyclopentyl-2-(4-methanesulfonyl-phenyl)-N-[5-(2-piperidin-1-yl-ethylsulfanyl)-thiazol-2-yl]-propionamide (Compound 23)

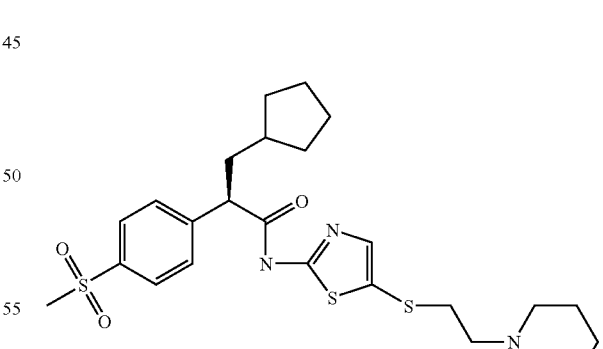

The title compound was prepared from (R)-3-cyclopentyl-2-(4-methanesulfonyl-phenyl)-N-(5-thiocyanato-thiazol-2-yl)-propionamide and 4-(2-chloroethyl)piperidine as described in Example 10. ¹H-NMR (CD₃OD): δ 7.92 (d, 2H), 7.67 (d, 2H), 7.54 (s, 1H), 3.96 (t, 1H), 3.48 (broad d, 2H), 3.28-3.03 (m, 2H), 3.10 (s, 3H), 3.07-3.03 (m, 2H), 2.91

(broad t, 2H), 2.26-2.29 (m, 1H), 1.92-1.45 (m, 14H), 1.18 (m, 2H); HPLC-MS: m/z: 522 (M+1).

Example 24

(R)-3-{2-[3-Cyclopentyl-2-(4-methanesulfonyl-phenyl)propionylamino]-thiazol-5-ylsulfanyl}-propionic acid (Compound 24)

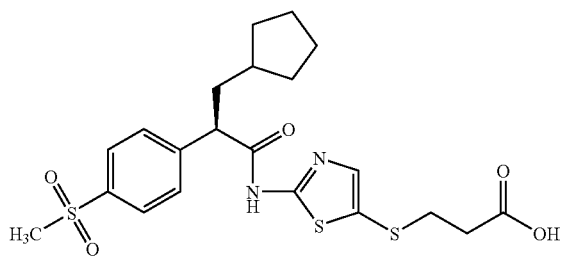

The title compound was prepared from (R)-3-{2-[3-cyclopentyl-2-(4-methanesulfonyl-phenyl)-propionylamino]-thiazol-5-ylsulfanyl}-propionic acid ethyl ester as described in Example 6. $^1$H-NMR (CD$_3$OD): δ 7.92 (d, 2H), 7.67 (d, 2H), 7.42 (s, 1H), 3.97 (t, 1H), 3.10 (s, 3H), 2.92 (t, 2H), 2.56 (t, 2H), 2.25-2.18 (m, 1H), 1.90-1.48 (m, 8H), 1.17 (m, 2H); HPLC-MS: m/z: 483 (M+1).

While the invention has been described and illustrated with reference to certain preferred embodiments thereof, those skilled in the art will appreciate that various changes, modifications. and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

The invention claimed is:

1. A compound of formula I:

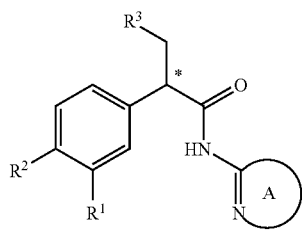

wherein, the * indicates an asymmetric atom;
$R^1$ is selected from the group consisting of H, Cl, F, Br, I, NH$_2$, —NHOH, —CN, —NO$_2$, C$_{1-6}$ alkyl, —OR$^5$, —C(O)OR$^6$, perfluoro-C$_{1-6}$ alkyl, C$_{1-6}$ alkyl-S—, perfluoro-C$_{1-6}$ alkyl-S—, C$_{1-6}$ alkyl-SO$_2$—, perfluoro-C$_{1-6}$ alkyl-SO$_2$—, C$_{1-6}$ alkoxy-C$_{1-6}$ alkyl-SO$_2$—, C$_{1-6}$ alkyl-S(O)—, and —SO$_2$NR$^{13}$R$^{14}$;

$R^2$ is selected from the group consisting of C$_{1-6}$ alkyl-SO$_2$—, C$_{3-6}$ cycloalkyl-SO$_2$—, perfluoro-C$_{1-6}$ alkyl-SO$_2$—, and C$_{1-6}$ alkoxy-C$_{1-6}$ alkyl-SO$_2$—;
$R^3$ is cyclopentyl;
ring A is a mono-substituted thiazole;
wherein the substituent is selected from the group consisting of —SCN, —(CH$_2$)$_{0-2}$—S(O)$_p$—(CH$_2$)$_{1-4}$—C(O)OR$^7$; —(CH$_2$)$_{0-2}$—S(O)$_p$—(CH$_2$)$_{1-4}$—C(O)OH; —(CH$_2$)$_{0-2}$—S(O)$_p$—(CH$_2$)$_n$—NR$^{10}$R$^{11}$; —(CH$_2$)$_{0-2}$—S(O)$_p$—(CH$_2$)$_n$—C(O)NR$^{10}$R$^{11}$; and —(CH$_2$)$_n$-5-6 membered heterocycle consisting of carbon atoms and 1-3 heteroatoms selected from S(O)$_p$, O, and N and is substituted with 0-1 C$_{1-4}$ alkyl; and, R$^7$, at each occurrence, is independently selected from the group consisting of C$_{1-4}$ alkyl and C$_{3-6}$ cycloalkyl;
$R^5$, at each occurrence, is independently selected from the group consisting of H, C$_{1-6}$ alkyl, and perfluoro-C$_{1-6}$ alkyl;
$R^6$, at each occurrence, is independently C$_{1-6}$ alkyl;
$R^8$, at each occurrence, is independently selected from the group consisting of H, C$_{1-8}$ alkyl, —(CH$_2$)$_n$—OH, —(CH$_2$)$_n$—C(O)OH, aryl, and 5-10 membered heteroaryl consisting of carbon atoms and 1-3 heteroatoms selected from S(O)$_p$, O, and N;
$R^9$, at each occurrence, is independently selected from the group consisting of H, C$_{1-8}$ alkyl, —(CH$_2$)$_n$—OH, —(CH$_2$)$_n$—C(O)OH, aryl, and 5-10 membered heteroaryl consisting of carbon atoms and 1-3 heteroatoms selected from S(O)$_p$, O, and N;
alternatively, $R^8$ and $R^9$, together with the nitrogen to which they are attached form a 5-6 membered heterocycle, consisting of, in addition to the nitrogen atom to which R$^8$ and R$^9$ are attached, carbon atoms and 0-2 heteroatoms selected from S(O)$_p$, O, and N;
$R^{10}$, at each occurrence, is independently selected from the group consisting of H; C$_{1-6}$ alkyl; —(CH$_2$)$_n$—OH; —(CH$_2$)$_n$—C(O)OH; —(CH$_2$)$_n$—C$_{3-8}$ cycloalkyl; —(CH$_2$)$_n$-aryl; —(CH$_2$)$_n$-5-10 membered heterocycle consisting of carbon atoms and 1-3 heteroatoms selected from S(O)$_p$, O, and N; —(CH$_2$)$_n$-5-10 membered heteroaryl consisting of carbon atoms and 1-3 heteroatoms selected from S(O)$_p$, O, and N; —(CH$_2$)$_p$—NHR$^7$; and —(CH$_2$)$_n$—NR$^7$R$^7$;
$R^{11}$, at each occurrence, is independently selected from the group consisting of H; C$_{1-6}$ alkyl; —(CH$_2$)$_n$—OH; —(CH$_2$)$_n$—C(O)OH; —(CH$_2$)$_n$—C$_{3-8}$ cycloalkyl; —(CH$_2$)$_n$-aryl; —(CH$_2$)$_n$-5-10 membered heterocycle consisting of carbon atoms and 1-3 heteroatoms selected from S(O)$_p$, O, and N; —(CH$_2$)$_n$-5-10 membered heteroaryl consisting of carbon atoms and 1-3 heteroatoms selected from S(O)$_p$, O, and N; —(CH$_2$)$_n$—NHR$^7$; and —(CH$_2$)$_n$—NR$^7$R$^7$;
alternatively, $R^{10}$ and $R^{11}$, together with the nitrogen to which they are attached form a 5-6 membered heterocycle, consisting of, in addition to the nitrogen atom to which R$^{10}$ and R$^{11}$ are attached, carbon atoms and 0-2 heteroatoms selected from S(O)$_p$, O, and N; and wherein the heterocycle thus formed is substituted with 0-2 R$^{12}$;
$R^{12}$, at each occurrence, is independently selected from the group consisting of C$_{1-6}$ alkyl, Cl, F, Br, I, NO$_2$, —CN, —(CH$_2$)$_n$—OH, —(CH$_2$)$_n$—C(O)OH, NR$^8$R$^9$, NHS(O)$_2$CH$_3$, S(O)$_2$CH$_3$, and S(O)$_2$NH$_2$;
$R^{13}$, at each occurrence, is independently selected from the group consisting of H and C$_{1-4}$ alkyl;
$R^{14}$, at each occurrence, is independently selected from the group consisting of H and C$_{1-4}$ alkyl;
p, at each occurrence, is selected from 0, 1, and 2; and n, at each occurrence, is independently selected from 0, 1, 2, 3, 4, 5, and 6 or a pharmaceutically acceptable salt thereof.

2. A compound of claim 1, wherein in ring A the substituent is selected from the group consisting of: —SCN, —S(O)$_2$—CH$_2$—C(O)OR$^7$; —S(O)$_2$—CH$_2$—C(O)OH; —S—CH$_2$—C(O)OR$^7$; —S—CH$_2$—CH$_2$—C(O)OR$^7$; —S—CH$_2$—C(O)OH; —S—CH$_2$—CH$_2$—C(O)OH; —S—(CH$_2$)$_2$—NR$^{10}$R$^{11}$; —S—CH$_2$—C(O)NR$^{10}$R$^{11}$; and piperazine; and, R$^7$, at each occurrence, is independently selected from C$_{1-2}$ alkyl.

3. A compound of claim 1 wherein n is 1.

4. A compound of claim 1 wherein n is 2.

5. A compound of claim 1, wherein R$^8$ and R$^9$, together with the nitrogen to which they are attached form a heterocycle selected from: piperazine, piperidine, homopiperazine, and morpholine.

6. A compound of claim 1, wherein R$^{10}$ and R$^{11}$, together with the nitrogen to which they are attached form a heterocycle selected from the group consisting of: piperidine, piperazine, homopiperazine, pyrrolidine, and morpholine.

7. A compound of claim 1, wherein the asymmetric carbon shown is in the R configuration.

8. A compound of claim 1 wherein
R$^1$ is selected from the group consisting of H, Cl, F, Br, I, perfluoro-C$_{1-6}$ alkyl, NO$_2$, NH$_2$, C$_{1-6}$ alkyl-SO$_2$—, and —SO$_2$NR$^{13}$R$^{14}$; and,
R$^2$ is C$_{1-6}$ alkyl-SO$_2$—.

9. A compound of claim 8, wherein R$^1$ is H.

10. A compound of claim 8, wherein R$^1$ is selected from the group consisting of Cl, CF$_3$, and CH$_3$.

11. A compound of claim 8, wherein R$^1$ is H and R$^2$ is CH$_3$—SO$_2$—.

12. A compound selected from the group consisting of:
3-Cyclopentyl-2-(4-methanesulfonyl-phenyl)-N-[5-(4-methyl-piperazin-1-yl)-thiazol-2-yl]-propionamide
{2-[3-Cyclopentyl-2-(4-methanesulfonyl-phenyl)-propionylamino]-thiazol-5-ylsulfanyl}-acetic acid ethyl ester
{2-[3-Cyclopentyl-2-(4-methanesulfonyl-phenyl)-propionylamino]-5-methyl-thiazol-4-yl}-acetic acid
{2-[3-Cyclopentyl-2-(4-methanesulfonyl-phenyl)-propionylamino]-thiazol-5-ylsulfanyl}-acetic acid
(R)-3-Cyclopentyl-2-(4-methanesulfonyl-phenyl)-N-(5-thiocyanato-thiazol-2-yl)-propionamide
(R)-3-Cyclopentyl-N-[5-(2-diethylamino-ethylsulfanyl)-thiazol-2-yl]-2-(4-methanesulfonyl-phenyl)-propionamide
(R)-3-Cyclopentyl-2-(4-methanesulfonyl-phenyl)-N-(5-methylsulfanyl-thiazol-2-yl)-propionamide
3-Cyclopentyl-N-(5-diethylcarbamoylmethylsulfanyl-thiazol-2-yl)-2-(4-methanesulfonyl-phenyl)-propionamide
{2-[3-Cyclopentyl-2-(4-methanesulfonyl-phenyl)-propionylamino]-thiazole-5-sulfonyl}-acetic acid
(R)-{2-[3-Cyclopentyl-2-(4-methanesulfonyl-phenyl)-propionylamino]-thiazol-5-ylsulfanyl}-acetic acid ethyl ester
(R)-{2-[3-Cyclopentyl-2-(4-methanesulfonyl-phenyl)-propionylamino]-thiazol-5-ylsulfanyl}-acetic acid
(R)-3-{2-[3-Cyclopentyl-2-(4-methanesulfonyl-phenyl)-propionylamino]-thiazol-5-ylsulfanyl}-propionic acid ethyl ester
(R)-3-Cyclopentyl-2-(4-methanesulfonyl-phenyl)-N-[5-(2-oxo-2-piperazin-1-yl-ethylsulfanyl)-thiazol-2-yl]-propionamide
(R)-3-Cyclopentyl-2-(4-methanesulfonyl-phenyl)-N-[5-(2-morpholin-4-yl-2-oxo-ethylsulfanyl)-thiazol-2-yl]-propionamide
(R)-3-Cyclopentyl-2-(4-methanesulfonyl-phenyl)-N-{5-[2-(4-methyl-piperazin-1-yl)-2-oxo-ethylsulfanyl]-thiazol-2-yl}-propionamide
(R)-3-Cyclopentyl-2-(4-methanesulfonyl-phenyl)-N-[5-(2-oxo-2-piperidin-1-yl-ethylsulfanyl)-thiazol-2-yl]-propionamide
(R)-3-Cyclopentyl-N-[5-(2-dimethylamino-ethylsulfanyl)-thiazol-2-yl]-2-(4-methanesulfonyl-phenyl)-propionamide
(R)-3-Cyclopentyl-2-(4-methanesulfonyl-phenyl)-N-[5-(2-morpholin-4-yl-ethylsulfanyl)-thiazol-2-yl]-propionamide
(R)-3-Cyclopentyl-2-(4-methanesulfonyl-phenyl)-N-[5-(2-piperidin-1-yl-ethylsulfanyl)-thiazol-2-yl]-propionamide
(R)-3-{2-[3-Cyclopentyl-2-(4-methanesulfonyl-phenyl)-propionylamino]-thiazol-5-ylsulfanyl}-propionic acid
(R)-3-Cyclopentyl-2-(4-methanesulfonyl-phenyl)-N-[5-(4-methyl-piperazin-1-yl)-thiazol-2-yl]-propionamide
(R)-{2-[3-Cyclopentyl-2-(4-methanesulfonyl-phenyl)-propionylamino]-thiazol-5-ylsulfanyl}-acetic acid ethyl ester
(R)-{2-[3-Cyclopentyl-2-(4-methanesulfonyl-phenyl)-propionylamino]-thiazol-5-ylsulfanyl}-acetic acid
(R)-3-Cyclopentyl-N-(5-diethylcarbamoylmethylsulfanyl-thiazol-2-yl)-2-(4-methanesulfonyl-phenyl)-propionamide
or a pharmaceutically acceptable salt thereof.

13. A pharmaceutical composition comprising: a pharmaceutically acceptable carrier and a compound of claim 1 or a pharmaceutically acceptable salt thereof.

* * * * *